United States Patent
Hartman

(10) Patent No.: US 10,632,112 B2
(45) Date of Patent: Apr. 28, 2020

(54) COMBINATION THERAPY FOR TREATMENT OF HBV INFECTIONS

(71) Applicant: Novira Therapeutics Inc., Doylestown, PA (US)

(72) Inventor: George D. Hartman, Lansdale, PA (US)

(73) Assignee: NOVIRA THERAPEUTICS, INC., Doylestown, PA (US)

( * ) Notice: Subject to any disclaimer, the term of this patent is extended or adjusted under 35 U.S.C. 154(b) by 0 days.

(21) Appl. No.: 16/235,210

(22) Filed: Dec. 28, 2018

(65) Prior Publication Data

US 2019/0209541 A1 Jul. 11, 2019

Related U.S. Application Data

(63) Continuation of application No. 15/284,807, filed on Oct. 4, 2016, now Pat. No. 10,213,420, which is a continuation of application No. 14/615,292, filed on Feb. 5, 2015, now abandoned.

(60) Provisional application No. 61/936,242, filed on Feb. 5, 2014.

(51) Int. Cl.
| | |
|---|---|
| *A61K 31/45* | (2006.01) |
| *A61K 38/21* | (2006.01) |
| *A61K 31/445* | (2006.01) |
| *A61K 31/397* | (2006.01) |
| *A61K 31/40* | (2006.01) |

(52) U.S. Cl.
CPC ............ *A61K 31/45* (2013.01); *A61K 31/397* (2013.01); *A61K 31/40* (2013.01); *A61K 31/445* (2013.01); *A61K 38/21* (2013.01); *A61K 38/212* (2013.01)

(58) Field of Classification Search
None
See application file for complete search history.

(56) References Cited

U.S. PATENT DOCUMENTS

| | | |
|---|---|---|
| 3,843,662 A | 10/1974 | Holland |
| 4,569,940 A | 2/1986 | Watts |
| 4,962,101 A | 10/1990 | Dininno et al. |
| 4,995,898 A | 2/1991 | Nasu et al. |
| 5,272,167 A | 12/1993 | Girijavallabhan et al. |
| 5,308,826 A | 5/1994 | Chin et al. |
| 5,314,880 A | 5/1994 | Whittaker et al. |
| 5,571,821 A | 11/1996 | Chan et al. |
| 5,585,327 A | 12/1996 | Chin et al. |
| 5,607,929 A | 3/1997 | Nicol |
| 5,708,034 A | 1/1998 | Kleemann et al. |
| 5,723,411 A | 3/1998 | Stevenson |
| 5,756,524 A | 5/1998 | Riordan et al. |
| 5,795,907 A | 8/1998 | Kalindjian et al. |
| 5,912,260 A | 6/1999 | Kalindjian et al. |
| 5,919,970 A | 7/1999 | Song et al. |
| 5,939,423 A | 8/1999 | Karlin |
| 6,025,367 A | 2/2000 | Forbes et al. |
| 6,265,408 B1 | 7/2001 | Forbes et al. |
| 6,476,025 B1 | 11/2002 | Flockerzi et al. |
| 6,650,463 B2 | 11/2003 | Obikawa et al. |
| 6,668,527 B2 | 12/2003 | Chupak et al. |
| 6,780,389 B2 | 8/2004 | Karl et al. |
| 7,115,595 B2 | 10/2006 | Sunagawa et al. |
| 7,186,735 B2 | 3/2007 | Strobel et al. |
| 7,338,956 B2 | 3/2008 | Strobel et al. |
| 7,348,324 B2 | 3/2008 | Imamura et al. |
| 7,368,457 B2 | 5/2008 | Josien et al. |
| 7,384,967 B2 | 6/2008 | Polisetti et al. |
| 7,576,688 B2 | 1/2009 | Suzuki et al. |
| 7,541,373 B2 | 6/2009 | Polisetti et al. |
| 7,544,700 B2 | 6/2009 | Halazy et al. |
| 7,595,322 B2 | 9/2009 | Morgan et al. |
| 7,608,723 B2 | 10/2009 | Boyce et al. |
| 7,750,158 B2 | 7/2010 | Shankar et al. |
| 7,786,104 B2 | 8/2010 | Dubois et al. |
| 7,790,726 B2 | 9/2010 | Zhang et al. |
| 7,838,525 B2 | 11/2010 | Jones et al. |
| 7,888,373 B2 | 2/2011 | Morgan et al. |
| 7,994,168 B2 | 8/2011 | Lennig et al. |
| 8,071,779 B2 | 12/2011 | Richards et al. |
| 8,084,457 B2 | 12/2011 | Choidas et al. |
| 8,097,728 B2 | 1/2012 | Gu et al. |
| 8,101,620 B2 | 1/2012 | Morgan et al. |
| 8,143,269 B2 | 3/2012 | Whitten et al. |
| 8,153,650 B2 | 4/2012 | Dubois et al. |
| 8,153,803 B2 | 4/2012 | Kazantsev et al. |
| 8,207,195 B2 | 6/2012 | Navratil et al. |

(Continued)

FOREIGN PATENT DOCUMENTS

| | | |
|---|---|---|
| CA | 2950807 A1 | 12/2015 |
| CN | 102093320 A | 6/2011 |

(Continued)

OTHER PUBLICATIONS

The Merck Index (2013) "Infliximab," An Encyclopedia of Chemicals, Drugs and Biologicals. 14th Ed. p. 924.
The Merck Index (2013) "Zidovudine," An Encyclopedia of Chemicals, Drugs and Biologicals. 14th Ed. p. 1885.
Thompson et al. (2007) "Toll-like receptors, RIG-I-like RNA helicases and the antiviral innate immune response," Immunology and Cell Biology. 85:435-445.
Weber et al. (2002) "Inhibition of human hepatitis B virus (HBV) by a novel non-nucleosidic compound in a transgenic mouse model," Antiviral Res. 54:69-78.
West (1984) Solid State Chemistry and its Applications. John Wiley & Sons. pp. 33-36.

(Continued)

*Primary Examiner* — James D. Andereson
*Assistant Examiner* — Stephanie K Springer
(74) *Attorney, Agent, or Firm* — Brian C. Trinque; Lathrop GPM LLP

(57) ABSTRACT

Provided herein is a combination therapy comprising a compound of Formula I and peginterferon alfa-2a, or another interferon analog. The combination therapy is useful for the treatment of HBV infection. Also provided herein are compositions comprising a compound of Formula I and peginterferon alfa-2a, or another interferon analog.

16 Claims, 2 Drawing Sheets

(56) References Cited

U.S. PATENT DOCUMENTS

| | | |
|---|---|---|
| 8,227,489 B2 | 7/2012 | Dubois et al. |
| 8,273,754 B2 | 9/2012 | Hill et al. |
| 8,299,096 B2 | 10/2012 | Navratil et al. |
| 8,299,114 B2 | 10/2012 | Dubois et al. |
| 8,354,425 B2 | 1/2013 | Dubois et al. |
| 8,394,820 B2 | 3/2013 | Dubois et al. |
| 8,399,491 B2 | 3/2013 | Dubois et al. |
| 8,404,747 B2 | 3/2013 | Kazantsev et al. |
| 8,410,141 B2 | 4/2013 | Murata et al. |
| 8,410,147 B2 | 4/2013 | Peterson et al. |
| 8,536,168 B2 | 9/2013 | Dai et al. |
| 8,609,668 B2 | 12/2013 | Cuconati et al. |
| 8,629,274 B2 | 1/2014 | Hartman et al. |
| 8,722,742 B2 | 5/2014 | Reyes et al. |
| 8,808,702 B2 | 8/2014 | Reddy et al. |
| 8,889,716 B2 | 11/2014 | Prime et al. |
| 8,993,771 B2 | 3/2015 | Hartman et al. |
| 9,051,296 B2 | 6/2015 | Yamagishi et al. |
| 9,061,008 B2 | 6/2015 | Hartman et al. |
| 9,066,932 B2 | 6/2015 | Hartman et al. |
| 9,115,101 B2 | 8/2015 | Bodil Van Niel et al. |
| RE45,670 E | 9/2015 | Polisetti et al. |
| 9,169,212 B2 | 10/2015 | Hartman et al. |
| 9,181,288 B2 | 11/2015 | Hartman et al. |
| 9,205,079 B2 | 12/2015 | Hartman et al. |
| 9,339,510 B2 | 5/2016 | Hartman et al. |
| 9,400,280 B2 | 7/2016 | Hartman |
| 9,458,176 B2 | 10/2016 | Takaishi et al. |
| 9,505,722 B2 | 11/2016 | Hartman et al. |
| 9,567,299 B2 | 2/2017 | Vandyck et al. |
| 9,579,313 B2 | 2/2017 | Hartman |
| 9,676,747 B2 | 6/2017 | Hartman et al. |
| 10,081,627 B2 | 9/2018 | Guo et al. |
| 10,160,743 B2 | 12/2018 | Vandyck et al. |
| 10,196,376 B2 | 2/2019 | Hartman et al. |
| 2002/0049236 A1 | 4/2002 | Chupak et al. |
| 2004/0039009 A1 | 2/2004 | Jagtap et al. |
| 2004/0110802 A1 | 6/2004 | Thorarensen et al. |
| 2005/0009871 A1 | 1/2005 | Ramesh et al. |
| 2005/0054850 A1 | 3/2005 | Wu et al. |
| 2005/0129833 A1 | 6/2005 | Kincaid et al. |
| 2005/0148632 A1 | 7/2005 | Tokumasu et al. |
| 2005/0239833 A1 | 10/2005 | Kazantsev et al. |
| 2006/0040984 A1 | 2/2006 | Luckhurst et al. |
| 2006/0100228 A1 | 5/2006 | Shankar et al. |
| 2006/0100257 A1 | 5/2006 | Muto et al. |
| 2006/0122236 A1 | 6/2006 | Wood et al. |
| 2007/0142440 A1 | 6/2007 | Burgdorf et al. |
| 2007/0161578 A1 | 7/2007 | Hwa et al. |
| 2009/0018118 A1 | 1/2009 | Urleb et al. |
| 2009/0325960 A1 | 1/2009 | Fulcher et al. |
| 2009/0036420 A1 | 2/2009 | Galley et al. |
| 2009/0105218 A1 | 4/2009 | Ulven et al. |
| 2009/0163545 A1 | 6/2009 | Goldfarb |
| 2009/0259044 A1 | 10/2009 | Kazantsev |
| 2009/0325959 A1 | 12/2009 | Vittitow et al. |
| 2010/0008968 A1 | 1/2010 | Vittitow et al. |
| 2010/0016310 A1 | 1/2010 | Ingraham |
| 2010/0022517 A1 | 1/2010 | Richards et al. |
| 2010/0204210 A1 | 8/2010 | Sorensen et al. |
| 2011/0009622 A1 | 1/2011 | Jitsuoka et al. |
| 2011/0064695 A1 | 3/2011 | Qiu et al. |
| 2011/0064696 A1 | 3/2011 | Or et al. |
| 2011/0184019 A1 | 6/2011 | Zitzmann et al. |
| 2011/0189771 A1 | 8/2011 | Block et al. |
| 2011/0275630 A1 | 11/2011 | Matulenko et al. |
| 2011/0301158 A1 | 12/2011 | Polisetti et al. |
| 2013/0005756 A1 | 1/2013 | Vittitow et al. |
| 2013/0131059 A1 | 5/2013 | Lampe et al. |
| 2013/0131106 A1 | 5/2013 | Lampe et al. |
| 2013/0142827 A1 | 6/2013 | Block et al. |
| 2013/0203733 A1 | 9/2013 | Kazantsev et al. |
| 2013/0251673 A1 | 9/2013 | Hartman et al. |
| 2013/0267517 A1 | 10/2013 | Guo et al. |
| 2013/0303552 A1 | 11/2013 | Xu et al. |
| 2014/0178337 A1 | 6/2014 | Hartman et al. |
| 2014/0179665 A1 | 6/2014 | Hartman et al. |
| 2014/0275167 A1 | 9/2014 | Hartman |
| 2015/0152073 A1 | 6/2015 | Hartman et al. |
| 2015/0174115 A1 | 6/2015 | Hartman et al. |
| 2015/0175602 A1 | 6/2015 | Brown et al. |
| 2015/0197493 A1 | 7/2015 | Hartman |
| 2015/0197533 A1 | 7/2015 | Hartman et al. |
| 2015/0216938 A1 | 8/2015 | Hartman |
| 2015/0259324 A1 | 9/2015 | Hartman et al. |
| 2015/0266890 A1 | 9/2015 | Vandyck et al. |
| 2015/0274652 A1 | 10/2015 | Hartman |
| 2015/0274653 A1 | 10/2015 | Vandyck et al. |
| 2016/0000812 A1 | 1/2016 | Hartman et al. |
| 2016/0002155 A1 | 1/2016 | Vandyck et al. |
| 2016/0051512 A1 | 2/2016 | Vandyck et al. |
| 2016/0115125 A1 | 4/2016 | Vandyck et al. |
| 2016/0158214 A1 | 6/2016 | Hartman |
| 2016/0176817 A1 | 6/2016 | Vandyck et al. |
| 2016/0272599 A1 | 9/2016 | Hartman et al. |
| 2016/0347741 A1 | 12/2016 | Vandyck et al. |
| 2017/0002025 A1 | 1/2017 | Vendeville et al. |
| 2017/0015629 A1 | 1/2017 | Hartman et al. |
| 2017/0114018 A1 | 4/2017 | Hartman |
| 2017/0158634 A1 | 6/2017 | Vandyck et al. |
| 2017/0340642 A1 | 11/2017 | Hartman et al. |

FOREIGN PATENT DOCUMENTS

| | | |
|---|---|---|
| CN | 102206172 A | 10/2011 |
| EP | 0 232 067 A2 | 8/1987 |
| EP | 0 742 200 B1 | 7/1999 |
| EP | 2 280 001 A1 | 2/2011 |
| JP | S62-142164 A | 6/1987 |
| JP | 2008-525406 A | 7/2008 |
| JP | 2008-179621 A | 8/2008 |
| JP | 2010-535172 A | 11/2010 |
| RU | 2012112128 A | 10/2013 |
| WO | 1984/003281 A1 | 8/1984 |
| WO | 1992/007835 A1 | 5/1992 |
| WO | 1998/023285 A1 | 6/1998 |
| WO | 1999/009022 A1 | 2/1999 |
| WO | 1999/038845 A1 | 8/1999 |
| WO | 1999/048492 A1 | 9/1999 |
| WO | 1999/065906 A1 | 12/1999 |
| WO | 2001/005390 A2 | 1/2001 |
| WO | 2001/019788 A2 | 3/2001 |
| WO | 2001045712 A1 | 6/2001 |
| WO | 2001/051487 A1 | 7/2001 |
| WO | 2001/055121 A1 | 8/2001 |
| WO | 2001/085694 A2 | 11/2001 |
| WO | 2002/051410 A2 | 7/2002 |
| WO | 2002/064618 A2 | 8/2002 |
| WO | 2003/007955 A2 | 1/2003 |
| WO | 2003002518 A1 | 1/2003 |
| WO | 2003/044016 A1 | 5/2003 |
| WO | 2003/101961 A1 | 12/2003 |
| WO | 2004/010943 A2 | 2/2004 |
| WO | 2004/011427 A2 | 2/2004 |
| WO | 2004/022060 A2 | 3/2004 |
| WO | 2004/058709 A1 | 7/2004 |
| WO | 2004/086865 A1 | 11/2004 |
| WO | 2004/099192 A2 | 11/2004 |
| WO | 2004/100947 A2 | 11/2004 |
| WO | 2005/016922 A2 | 2/2005 |
| WO | 2005/044797 A1 | 5/2005 |
| WO | 2005/087217 A1 | 9/2005 |
| WO | 2005/105785 A2 | 11/2005 |
| WO | 2005/115374 A1 | 12/2005 |
| WO | 2006/002133 A1 | 1/2006 |
| WO | 2006012642 A2 | 2/2006 |
| WO | 2006/024834 A1 | 3/2006 |
| WO | 2006/053109 A1 | 5/2006 |
| WO | 2006/067445 A2 | 6/2006 |
| WO | 2006/067446 A1 | 6/2006 |
| WO | 2006/123257 A2 | 11/2006 |
| WO | 2006/128129 A2 | 11/2006 |
| WO | 2006/128172 A2 | 11/2006 |
| WO | 2007/031791 A1 | 3/2007 |

(56) References Cited

FOREIGN PATENT DOCUMENTS

| | | |
|---|---|---|
| WO | 2007070556 A2 | 6/2007 |
| WO | 2008/011476 A2 | 1/2008 |
| WO | 2008/022171 A1 | 2/2008 |
| WO | 2008/093614 A1 | 8/2008 |
| WO | 2008/137794 A1 | 11/2008 |
| WO | 2008/154819 A1 | 12/2008 |
| WO | 209/016088 A1 | 2/2009 |
| WO | 2009018219 A2 | 2/2009 |
| WO | 2009/062402 A1 | 5/2009 |
| WO | 2009/086303 A2 | 7/2009 |
| WO | 2009/146013 A1 | 12/2009 |
| WO | 2009/131065 A1 | 2/2010 |
| WO | 2010/018113 A2 | 2/2010 |
| WO | 2010/043592 A1 | 4/2010 |
| WO | 2010059658 A1 | 5/2010 |
| WO | 2010/088000 A2 | 8/2010 |
| WO | 2010/123139 A1 | 10/2010 |
| WO | 2011/002635 A1 | 1/2011 |
| WO | 2011/035143 A2 | 3/2011 |
| WO | 2011/088015 A1 | 7/2011 |
| WO | 2011/088561 A1 | 7/2011 |
| WO | 2011/109237 A2 | 9/2011 |
| WO | 2011/112191 A1 | 9/2011 |
| WO | 2011/123609 A1 | 10/2011 |
| WO | 2011/140324 A1 | 11/2011 |
| WO | 2011/155898 A1 | 12/2011 |
| WO | 2012/016133 A2 | 2/2012 |
| WO | 2012/018635 A2 | 2/2012 |
| WO | 2012/033956 A1 | 3/2012 |
| WO | 2012/049277 A1 | 4/2012 |
| WO | 2012/075235 A1 | 6/2012 |
| WO | 2012/080050 A1 | 6/2012 |
| WO | 2012/117216 A1 | 9/2012 |
| WO | 2012/136834 A1 | 10/2012 |
| WO | 2013/006394 A1 | 1/2013 |
| WO | 2013/096744 A1 | 6/2013 |
| WO | 2013/102655 A1 | 7/2013 |
| WO | 2013/130703 A2 | 9/2013 |
| WO | 2013144129 A1 | 10/2013 |
| WO | 2013174962 A1 | 11/2013 |
| WO | 2013/181584 A2 | 12/2013 |
| WO | 2013/184757 A1 | 12/2013 |
| WO | 2014/033167 A1 | 3/2014 |
| WO | 2014/033170 A1 | 3/2014 |
| WO | 2014/033176 A1 | 3/2014 |
| WO | 2014/037480 A1 | 3/2014 |
| WO | 2014/106019 A2 | 7/2014 |
| WO | 2014/131847 A1 | 9/2014 |
| WO | 2014/151958 A1 | 9/2014 |
| WO | 2014/161888 A1 | 10/2014 |
| WO | 2014165128 A2 | 10/2014 |
| WO | 2014/184350 A1 | 11/2014 |
| WO | 2014/184365 A1 | 11/2014 |
| WO | 2014184328 A1 | 11/2014 |
| WO | 2014/191301 A1 | 12/2014 |
| WO | 2014/191726 A1 | 12/2014 |
| WO | 2014/198880 A1 | 12/2014 |
| WO | 2015/011281 A1 | 1/2015 |
| WO | 2015/055764 A1 | 4/2015 |
| WO | 2015/057945 A1 | 4/2015 |
| WO | 2015/059212 A1 | 4/2015 |
| WO | 2015/073774 A1 | 5/2015 |
| WO | 2015/109130 A1 | 7/2015 |
| WO | 2015/116923 A1 | 8/2015 |
| WO | 2015118057 A1 | 8/2015 |
| WO | 2015/138895 A1 | 9/2015 |
| WO | 2015/144093 A1 | 10/2015 |
| WO | 2015/180631 A1 | 12/2015 |
| WO | 2016/089990 A1 | 6/2016 |
| WO | 2016/109663 A2 | 7/2016 |
| WO | 2016/109684 A2 | 7/2016 |
| WO | 2016/109689 A2 | 7/2016 |
| WO | 2016/113273 A1 | 7/2016 |
| WO | 2016/149581 A1 | 9/2016 |
| WO | 2016/161268 A1 | 10/2016 |
| WO | 2016/168619 A1 | 10/2016 |
| WO | 2016/183266 A1 | 11/2016 |
| WO | 2015132276 A1 | 11/2018 |

OTHER PUBLICATIONS

Yarmolchuk (2011) "Synthesis of β-fluoro-β-proline," Tetrahedron Letters. 51(12):1300-1302.

Zhang et al. (2005) "A Potent Small Molecule Inhibits Polyglutamine Aggregation in Huntington's Disease Neurons and Suppresses Neurodegeneration in vivo," Proc. Natl. Acad. Sci. USA. 102(3):892-897.

Carver, et al., Polyfunctionalisation of Imidazole via Sequential Imidazolyl Anion Formation, Tetrahedron, 1997, pp. 14481-14496, vol. 53 Issue 42.

Geng et al., "Small-Molecule Inhibitors for the Treatment of Hepatitis B Virus Documented in Patents", Mini-Reviews in Medicinal Chemistry, Apr. 1, 2013, pp. 749-776 (XP055105561-XP009176654), vol. 13.

Goodman, et al, "Discovery of potent, selective sulfonylfuran urea endothelial lipase inhibitors", Bioorganic & Medicinal Chemistry Letters, vol. 19:pp. 27-30 (2009).

Hughes, et al., "Hepatitis Delta Virus", The Lancet, vol. 378: pp. 73-85, (Jul. 2, 2011).

Jayathilaka, et al, "A chemical compound that stimulated the human homologous recombination protein RAD51", Proceedings of the National Academy of Sciences on the United States of America, vol. 105 (41): pp. 15848-15853 (Oct. 14, 2008).

Li Bing, et al., Progress in anti Hepatitis B Virus non-nucleosidic drugs, J. Liaoning Medical University, vol. 30(1): pp. 88-91 (Dec. 31, 2009.).

Liu et al, discovery of Highly Potent and Selective Pan-Aurora Kinase Inhibitors with Enhanced in Vivo Antitumor Therapeutic Index, Journal of Medicinal chemistry, Mar. 1, 2012, pp. 3250-3260, vol. 55.

Online Registry via STN , Aug. 13, 2012, RN 1390589-54-4.
Online Registry via STN 2010, RN 1253220-91-5.
Online Registry via STN Aug. 12, 2012, RN 1389720-57-3.
Online Registry via STN Aug. 13, 2012, RN 1390500-09-0.
Online Registry via STN Aug. 30, 2011, RN 1325664-90-1.
Online Registry via STN Dec. 22, 2008, RN 1088200-12-7.
Online Registry via STN Dec. 8, 2012, RN 1389686-79-6.
Online Registry via STN Feb. 2, 2007, RN 919040-394.
Online Registry via STN Feb. 2, 2007, RN 919040-53-2.
Online Registry via STN Feb. 2, 2007, RN 919040-554.
Online Registry via STN Jan. 16, 2001, RN 314043-17-9.
Online Registry via STN Jul. 6, 2012, RN 1375909-37-7.
Online Registry via STN Jun. 8, 2012. RN 1386725-02-5.
Online Registry via STN Mar. 17, 2013, RN 1424462-66-7.
Online Registry via STN Nov. 12, 2007, RN 957487-45-5.
Online Registry via STN Nov. 12, 2007, RN 957487-49-9.
Online Registry via STN Oct. 10, 2001, RN 361373-90-2.
Online Registry via STN Sep. 18, 2012, RN 1394742-82-5.
Online Registry via STN, Apr. 24, 2002, RN 406926-60-1.
Online Registry via STN, Apr. 28, 2011, RN 1286906-97-5.
Online Registry via STN, Dec. 28, 2008, RN 1090750-88-1.
Online Registry via STN, Feb. 15, 2007, RN 921179-95-5.
Online Registry via STN, Feb. 2, 2007, RN 9019040-48-5.
Online Registry via STN, Feb. 2, 2007, RN 919040-37-2.
Online Registry via STN, Feb. 3, 2007, RN 924514-21-6.
Online Registry via STN, Feb. 9, 2003, RN 577752-12-6.
Online Registry via STN, Jan. 24, 2008, RN 296790-26-6.
Online Registry via STN, Jun. 9, 2011, RN 1328738-57-3.
Online Registry via STN, Mar. 17, 2003, RN 499189-09-2.
Online Registry via STN, Sep. 1, 2001, RN 313253-89-3.
Online Registry via STN. Apr. 19, 2008, RN 930914-71-9.

Patel, et al., "Synthesis N-Ethylpiperazinyl Sulfonyl Group Incorporated Benzamides", Indian Journal of Heterocyclic Chemistry, vol. 15: pp. 201-202 (Oct.-Dec. 2005).

Qidong You et al, Pharmaceutical Chemistry, Chemical Industry Press, Jan. 31, 2014, pp. 32-31.

(56) References Cited

OTHER PUBLICATIONS

Qiu, et al, "Antihepatitis B therapy: a review of current medications and novel small molecule inhibitors", Fudamental & Clinical Pharmacology, pp. 1-18 (XP055105340) (Nov. 1, 2013).
Schroder, et al., "Arzneimittelchemie Passage", Arzneimittelchemei Grundlagen Nerven Musklen and Gewebe, vol. XX (XX): pp. 30-33 (Jan. 1, 1976).
Stalder, et al, "Selective antagonists of mouse trace amine-associated receptor 1 (mTAAR1): Discovery of EPPTB (RO5212773)", Bioorganic & Medicinal Chemistry Letters, vol. 21: pp. 1227-1231 (Dec. 21, 2010).
Wang, et al., "Synthesis and Evaluation of Benzothiazole-Based Analogues as Novel, Potent, and Selective Fatty Acid Amide Hydrolase Inhibitors", J. Med. Chem., vol. 52: pp. 170-180 (2009).
Brahmania (Jan. 13, 2016) "New therapeutic agents for chronic hepatitis B," Lancet Infect. Dis. 16(2):e10-e21.
Brezillon et al. (2011) "Antiviral activity of Bay 41-4109 on hepatitis B virus in humanized Alb-uPA/SCID mice," PLoS One. 6:e25096. pp. 1-6.
Chang et al. (2007) "NMR-spectroscopy-based metabonomic approach to the analysis of Bay41-4109, a novel anti-HBV compound, induced hepatotoxicity in rats," Tox. Letters. 173:161-167.
Cho et al. (Dec. 25, 2013) "2-amino-N-(2,6-dichloropyridin-3-yl)acetamide derivatives as a novel class of HBV capsid assembly inhibitor," Viral Hep. 21:843-852.
Cowie et al. (Jun. 11, 2013) "Mortality due to viral hepatitis in the Global Burden of Disease Study 2010: new evidence of an urgent global public health priority demanding action," Antivir. Ther. 18:953-954.
Delaney et al. (2002) "Phenylpropenamide derivatives AT-61 and AT-130 inhibit replication of wild-type and lamivudine-resistant strains of hepatitis B virus in vitro," Antimicrob. Agents Chemother. 46:3057-3060.
Deres et al. (2003) "Inhibition of hepatitis B virus replication by drug-induced depletion of nucleocapsids," Science. 299:893-896.
Gane (2014) "Phase 1a Saftey and Pharmacokinetics of NVR 3-778, a Potential First-in-Class HBV Core Inhibitor," In; The Abstracts of the Liver Meeting 2014 (AASLD). Boston, MA. Abstract LB-19.
Guo (2011) "HBc binds to the CpG islands of HBV cccDNA and promotes an epigenetic permissive state," Epigenetics. 6:720-726.
Huang et al. (Oct. 2016) "Blockage of HBV Virus Replication and Inhibition of cccDNA Establishment by Core Protein Allosteric Modifiers (CpAMs)," In; The Abstracts of the Liver Meeting 2016 (AASLD). Boston, MA. po. 937A-938A. Abstract 1897.
Katen et al. (Jul. 18, 2013) "Assembly-directed antivirals differentially bind quasiequivalent pockets to modify hepatitis B virus capsid tertiary and quaternary structure," Structure. 21(8):1406-1416.
Klumpp et al. (2015) "O115: High antiviral activity of the HBV core inhibitor NVR 3-778 in the humanized uPA/SCID mouse model," J. Hepatol. 62:S250.
Klumpp et al. (Nov. 23, 2015) "High-resolution crystal structure of a hepatitis B virus replication inhibitor bound to the viral core protein," Proc. Natl. Acad. Sci. 112:15196-15201.
Lam et al. (Oct. 2015) "Inhibition of Hepatitis B Virus Replication by the HBV Core Inhibitor NVR 3-778," In; The Abstracts of the Liver Meeting 2015 (AASLD). San Francisco, CA. p. 223A. Abstract 33.
Lam et al. (Oct. 2016) "HBV Core Assembly Modulators Block Antigen Production when Present during Infection, but not during Persistent Infection," In; The Abstracts of the Liver Meeting 2016 (AASLD). Boston, MA. p. 913A. Abstract 1850.
Lam et al. (Sep. 2016) "Serum HBV RNA as a Pharmacodynamic (PD) Marker of HBV Treatment Response to Core Assembly Modulator NVR 3-778 and Pegylated-Interferon Alpha," Poster Presented In; The AASLD/EASL HBV Treatment Endpoints Workshop. Alexandria, VA. Sep. 8-9, 2016. Poster No. 3774.
Lucifora et al. (Feb. 20, 2014) "Specific and nonhepatotoxic degradation of nuclear hepatitis B virus cccDNA," Science. 343:1221-1228.
Manzoor et al. (Nov. 28, 2015) "Hepatitis B virus therapy: What's the future holding for us?" World J Gastro. 21:12558-12575.
Qiu et al. (Aug. 10, 2016) "Design and Synthesis of Orally Bioavailable 4-Methyl Heteroaryldihydropyrimidine Based Hepatitis B Virus (HBV) Capsid Inhibitors," J. Med. Chem. 59:7651-7666.
Stray et al. (2005) "A heteroaryldihydropyrimidine activates and can misdirect hepatitis B virus capsid assembly," Proc. Natl. Acad. Sci. USA. 102:8138-8143.
Stray et al. (2006) "BAY 41/4109 has multiple effects on Hepatitis B virus capsid assembly," J. Mol. Recognit. 19:542-548.
Tan et al. (Jan. 2, 2013) "Genetically altering the thermodynamics and kinetics of hepatitis B virus capsid assembly has profound effects on virus replication in cell culture," J. Vir. 87:3208-3216.
Wang et al. (Jun. 6, 2012) "In vitro inhibition of HBV replication by a novel compound, GLS4, and its efficacy against adefovir-dipivoxil-resistant HBV mutations," Antiviral therapy 17:793-803.
Wang et al. (May 28, 2016) "Serum hepatitis B virus RNA is encapsidated pregenome RNA that may be associated with persistence of viral infection and rebound," J. Hepatol. 65:700-710.
Wu et al. (Aug. 19, 2013) "Preclinical characterization of GLS4, an inhibitor of hepatitis B virus core particle assembly," Antimicrob. Agents Chemother. 57:5344-5354.
Yang et al. (2016) "Effect of a hepatitis B virus inhibitor, NZ-4, on capsid formation," Antiviral Res. 125:25-33.
Yang et al. (Feb. 3, 2014) "Isothiafludine, a novel non-nucleoside compound, inhibits hepatitis B virus replication trough blocking pregenomic RNA encapsidation," Acta Pharmacol. Sin. 35:410-418.
Yofaratnam et al. (Oct. 2016) "Safety, Tolerability and Pharmacokinetics of JNJ-56136379, a Novel HBV Caspid Assembly Modulator, in Healthy Subjects," In; The Abstracts of the Liver Meeting 2016 (AASLD). Boston, MA. po. 930A-931A. Abstract 1881.
Yuen et al. (Apr. 2016) "NVR 3-778, a first-in-class HBV Core inhibitor, alone and incombination with Peg-interferon (PEGIFN), in treatment naive HBeAg-Positive patients: early reductions in HBV DNA and HBeAg," In; The Abstracts of the International Liver Congress (EASL). pp. S210-S211. Abstract LB-06.
Yuen et al. (Oct. 2015) "Phase 1b Efficacy and Safety of NVR 3-778, a First-In-Class HBV Core Inhibitor, in HBeAg-Positive Patients with Chronic HBV Infection," In; The Abstracts of the Liver Meeting 2015 (AASLD). San Francisco, CA. pp. 1385A-1386A Abstract LB-10.
Zlotnick et al. (Jun. 27, 2015) "Core protein: A pleiotropic keystone in the HBV lifecycle," Antiviral Research. 121:82-93.
Zoulim et al. (Jun. 15, 2016) "Current treatments for chronic hepatitis B virus infections," Curr. Opin. Virol. 18:109-116.
Campagna et al. (Apr. 10, 2013) "Sulfonamoylbenzamides Derivatives Inhibit the Assembly of Hepatitis B virus in Nucleocapsids," J. Virol. 87(12):6931-6942.
El-Sharief et al. (1987) "Synthesis of different types of chlorinated sulfonamides with expected insecticidal and bactericidal activities," Proceedings of the Indian National Science Academy, Part A: Physical Sciences. 53 (1):179-188.
Ermann et al. (2008) "Arylsulfonamide CB2 receptor agonists: SAR and optimization of CB2 selectivity," Bioorganic & Medicinal Chemistry Letters. 18(5):1725-1729.
International Search Report with Written Opinion corresponding to International Patent Application No. PCT/US2015/014663, dated Apr. 6, 2015.
Lambeng et al. (2007) "Arylsulfonamides as a new class of cannabinoid CB1 receptor ligands: Identification of a lead and initial SAR studies," Bioorganic & Medicinal Chemistry Letters. 17(1):272-277.
Lau et al. (2005) "Peginterferon Alfa-2a, Lamivudine, and the Combination for HBeAg-Positive Chronic Hepatitis B," The New England Journal of Medicine. 352(26):2682-2695.
Marcellin et al. (2004) "Peginterferon Alfa-2a Alone, Lamivudine Alone, and the Two in Combination in Patients with HBeAg-Negative Chronic Hepatitis B," New Engl. J. Med. 351(12):1206-1217.
Mohamed et al. (1986) "Synthesis of different types of chlorinated sulfonamides with expected insecticidal and antimicrobial activities," Acta Pharmaceutica Jugoslavica. 36(3):301-310.

(56) References Cited

OTHER PUBLICATIONS

Taylor et al. (Mar. 3, 2011) "A Brain-Permeable Small Molecule Reduces Neuronal Cholesterol by Inhibiting Activity of Sirtuin 2 Deacetylase," ACS Chemical Biology. 6:540-546.
[Online] CAS (STN), 148:183450, RN 296790-26-6.
[Online] Registry via STN, May 6, 2011, RN 1291044-81-9.
[Online] Registry via STN, Oct. 7, 2008, RN 1057788-44-9.
[Online] Registry via STN, Oct. 7, 2008, RN 1057871-39-2.
[Online] Registry via STN, Aug. 15, 2011, RN 1317923-24-2.
[Online] Registry via STN, Aug. 15, 2011, RN 1318022-74-0.
[Online] Registry via STN, May 18, 2011, RN 1296380-95-4.
[Online] Registry via STN, Feb. 13, 2017, RN 1208400-27-4.
[Online] Registry via STN, Oct. 18, 2000, RN 296894-70-7.
[Online] Registry via STN, Sep. 20, 2013, RN 1452780-00-5.
Bennes et al. (2001) "Recognition-induced control and acceleration of a pyrrole Diels-Alder reaction," Tetrahedron Letters. 42(12):2377-2380.
Berke et al. (Oct. 2016) "Caspid assembly modulator JNJ-56136379 prevents de novo infection of primary human hepatocytes with hepatitis B virus," In; The Abstracts of the Liver Meeting 2016 (AASLD). Boston, MA. p. 124A. Abstract 234.
Cai et al. (Aug. 2012) "Identification of Disubstituted Sulfonamide Compounds as specific Inhibitors of Hepatitis B Virus Covalently Closed Circular DNA Formation," Antimicrobial Agents and Chemotherapy. 56(8):4277-4288.
Duan et al. (2009) "2-Phenylquinazolin-4(3H)-one, a class of potent PDES inhibitors with high selectivity versus PDE6," Bioorganic and Medicinal Chemistry. 19(10):2777-2779.
El-Sayed (1998) "A Comparative Study of the Reactions of Thiophene-2-Carboxanilides and Related Compounds," Chemistry of Heterocyclic Compounds. 34(7):796-801.
Extended European Search Report corresponding to European Patent Application No. 12182076, dated Apr. 19, 2013.
Extended European Search Report corresponding to European Patent Application No. 13157232, dated Apr. 5, 2013.
Extended European Search Report corresponding to European Patent Application No. 13162131, dated Sep. 11, 2013.
Extended European Search Report corresponding to European Patent Application No. 13168291, dated Jun. 20, 2013.
Extended European Search Report corresponding to European Patent Application No. 13168295, dated Oct. 7, 2013.
Extended European Search Report corresponding to European Patent Application No. 13169574, dated Aug. 19, 2013.
Geies (1991) "Synthesis of Some Thiazolo-[3, 2=A]Pyrimidines," Phosphorous, Sulfur and Silicon and the Related Elements. 56(1-4):87-93.
Hogan (2009) "Aqueous Process Chemistry: The Preparation of Aryl Sulfonyl Chlorides," Organic Process Research and Development 13(5):875-879.
International Search Report with Written Opinion corresponding to International Patent Application No. PCT/EP2013/067821, dated Nov. 28, 2013.
International Search Report with Written Opinion corresponding to International Patent Application No. PCT/EP2013/067829, dated Jan. 10, 2014.
International Search Report with Written Opinion corresponding to International Patent Application No. PCT/EP2014/053858, dated May 28, 2014.
International Search Report with Written Opinion corresponding to International Patent Application No. PCT/EP2014/056601, dated Jun. 13, 2014.
International Search Report with Written Opinion corresponding to International Patent Application No. PCT/EP2014/060102, dated Jul. 7, 2014.
International Search Report with Written Opinion corresponding to International Patent Application No. PCT/EP2014/060132, dated Jun. 16, 2014.
International Search Report with Written Opinion corresponding to International Patent Application No. PCT/US2012/071195, dated Apr. 26, 2013.
International Search Report with Written Opinion corresponding to International Patent Application No. PCT/US2014/024509, dated Oct. 22, 2014.
International Search Report with Written Opinion corresponding to International Patent Application No. PCT/US2015/011663, dated Apr. 29, 2015.
International Search Report with Written Opinion corresponding to International Patent Application No. PCT/US2016/023066, dated May 11, 2016.
International Search Report with Written Opinion corresponding to International Patent Application No. PCT/US2016/054424, dated Nov. 21, 2016.
Kim et al. (Apr. 9, 2011) "Discovery of novel HCV polymerase inhibitors using pharmacophore-based virtual screening," Bioorganic and Medicinal Chemistry. 21(11):3329-3334.
Liaw et al. (2009) "Hepatitis B virus infection," Lancet. 373:582-592.
Mabrouck (2012) "Discovering Best Candidates for Hepatocellular Carcinoma (HCC) by in-Silica Techniques and Tools," International Journal of Bioinformatics Research and Applications. 8(1-2):141-152.
Patani et al. (1996) "Bioisosterism: A Rational Approach in Drug Design," Chem. Rev. 96:3147-3176.
Patel et al. (2005) "Synthesis N-ethylpiperazinyl Sulfonyl Group Incorporated Benzamides" Indian Journal of Heterocyclic Chemistry. 15:201-202.
Search Report with Written Opinion corresponding to Singapore Patent Application No. 11201402660Y, completed May 22, 2015.
Supplementary European Search Report corresponding to European Patent Application No. 12859684, dated May 27, 2015.

COMBINATION THERAPY FOR TREATMENT OF HBV INFECTIONS

RELATED APPLICATIONS

This application is a continuation of U.S. application Ser. No. 15/284,807, filed on Oct. 4, 2016, which is a continuation of U.S. application Ser. No. 14/615,292, filed Feb. 5, 2015, now abandoned, which application claims priority to U.S. Provisional Application No. 61/936,242, filed Feb. 5, 2014, now expired. The entire contents of these applications are incorporated herein by reference.

BACKGROUND

Chronic hepatitis B virus (HBV) infection is a significant global health problem, affecting over 5% of the world population (over 350 million people worldwide and 1.25 million individuals in the U.S.).

Despite the availability of a prophylactic HBV vaccine, the burden of chronic HBV infection continues to be a significant unmet worldwide medical problem, due to suboptimal treatment options and sustained rates of new infections in most parts of the developing world. Current treatments rarely provide a cure and are limited to only two classes of agents (interferon and nucleoside analogues/inhibitors of the viral polymerase); drug resistance, low cure rates, and tolerability issues limit their impact. The low cure rates of HBV can be attributed at least in part to incomplete suppression of HBV replication and to the presence and persistence of covalently closed circular DNA (cccDNA) in the nucleus of infected hepatocytes. However, persistent suppression of HBV DNA slows liver disease progression and helps to prevent hepatocellular carcinoma. Therefore, current therapy goals for HBV-infected patients are directed to reducing serum HBV DNA to low or undetectable levels, and to ultimately reducing or preventing the development of cirrhosis and hepatocellular carcinoma.

Although there is precedent for improved efficacy from combination regimens in other viral diseases such as HIV and HCV, combination of existing HBV drugs have failed to show improved efficacy. Neither the combinations of interferon α (IFN) and nucleos(t)ide polymerase inhibitors nor combinations of nucleos(t)ide polymerase inhibitors have provided improved efficacy in treating HBV compared to monotherapy.

Therefore, there remains a need in the art for improved therapies for treating HBV infection.

SUMMARY OF THE INVENTION

Provided herein is a combination therapy comprising a capsid assembly inhibitor and an interferon. The combination therapy is useful for the treatment of HBV infection. This combination unexpectedly provides additional HBV virus replication suppression efficacy compared to monotherapy with interferon, entecavir, or a compound of Formula I.

Accordingly, in one aspect, provided herein is a method of treating an HBV infection in a subject in need thereof, comprising administering to the subject a capsid assembly inhibitor and an interferon. In one embodiment, the interferon is selected from the group consisting of interferon alpha, interferon alpha-2a, recombinant interferon alpha-2a, peginterferon-alpha 2a, interferon alpha-2b, recombinant interferon alpha-2b, interferon alpha-2b XL, peginterferon alpha-2b, glycosylated interferon alpha-2b, interferon alpha-2c, recombinant interferon alpha-2c, interferon beta, interferon beta-1a, peginterferon beta-1a, interferon delta, interferon lambda, peginterferon lambda-1, interferon omega, interferon tau, gamma interferon, interferon alfacon-1, interferon alpha-n1, interferon alpha-n3, albinterferon alpha-2b, BLX-883, DA-3021, PEG-Infergen, and BELEROFON. In another embodiment, the interferon is selected from the group consisting of peginterferon alpha-2a, peginterferon alpha-2b, glycosylated interferon alpha-2b, peginterferon beta-1a, and peginterferon lambda-1. In a particular embodiment, the interferon is peginterferon alpha-2a.

In one embodiment of the method, the capsid assembly inhibitor is a compound of Formula I:

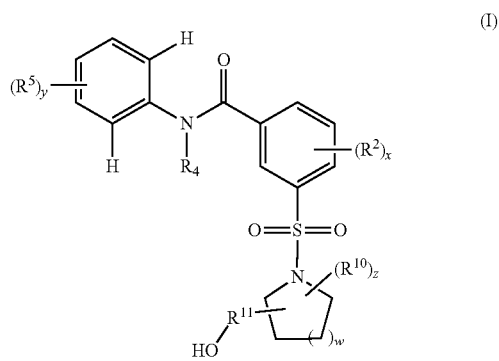

or a pharmaceutically acceptable salt thereof.

In another aspect, provided herein is a method of treating an HBV infection in a subject in need thereof, comprising administering to the subject peginterferon alfa-2a and a compound of Formula I:

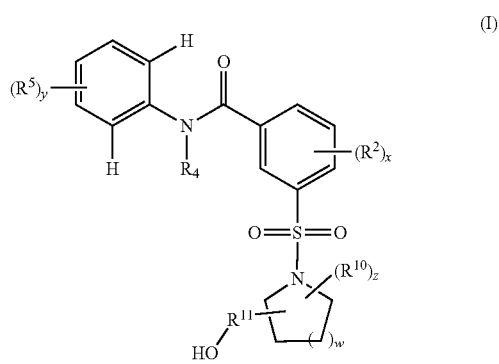

or a pharmaceutically acceptable salt thereof.

In an embodiment, the peginterferon alfa-2a and compound of Formula I are in a single formulation or unit dosage form. In another embodiment, this method further comprises a pharmaceutically acceptable carrier. In yet another embodiment, the peginterferon alfa-2a and compound of Formula I are administered separately. In still another embodiment, the method comprises administering the peginterferon alfa-2a and compound of Formula I at substantially the same time.

In another embodiment, the treatment comprises administering the peginterferon alfa-2a and compound of Formula I at different times. In one embodiment, the peginterferon alfa-2a is administered to the subject, followed by administration of a compound of Formula I. In another embodiment, the compound of Formula I is administered to the subject, followed by administration of the peginterferon alfa-2a. In still another embodiment, the peginterferon alfa-2a and compound of Formula I are in separate formulations or unit dosage forms.

In an embodiment of any of the above methods, the subject is human.

In an aspect, provided herein is a composition comprising peginterferon alfa-2a and a compound of Formula I:

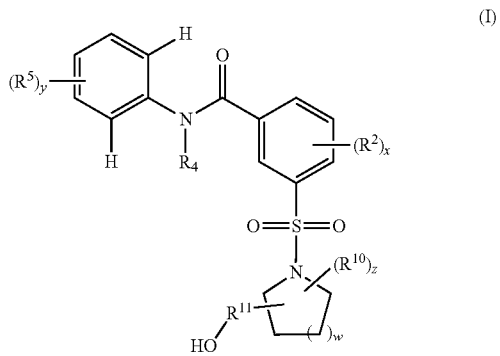

(I)

or a pharmaceutically acceptable salt thereof.

DETAILED DESCRIPTION

Figure 1:
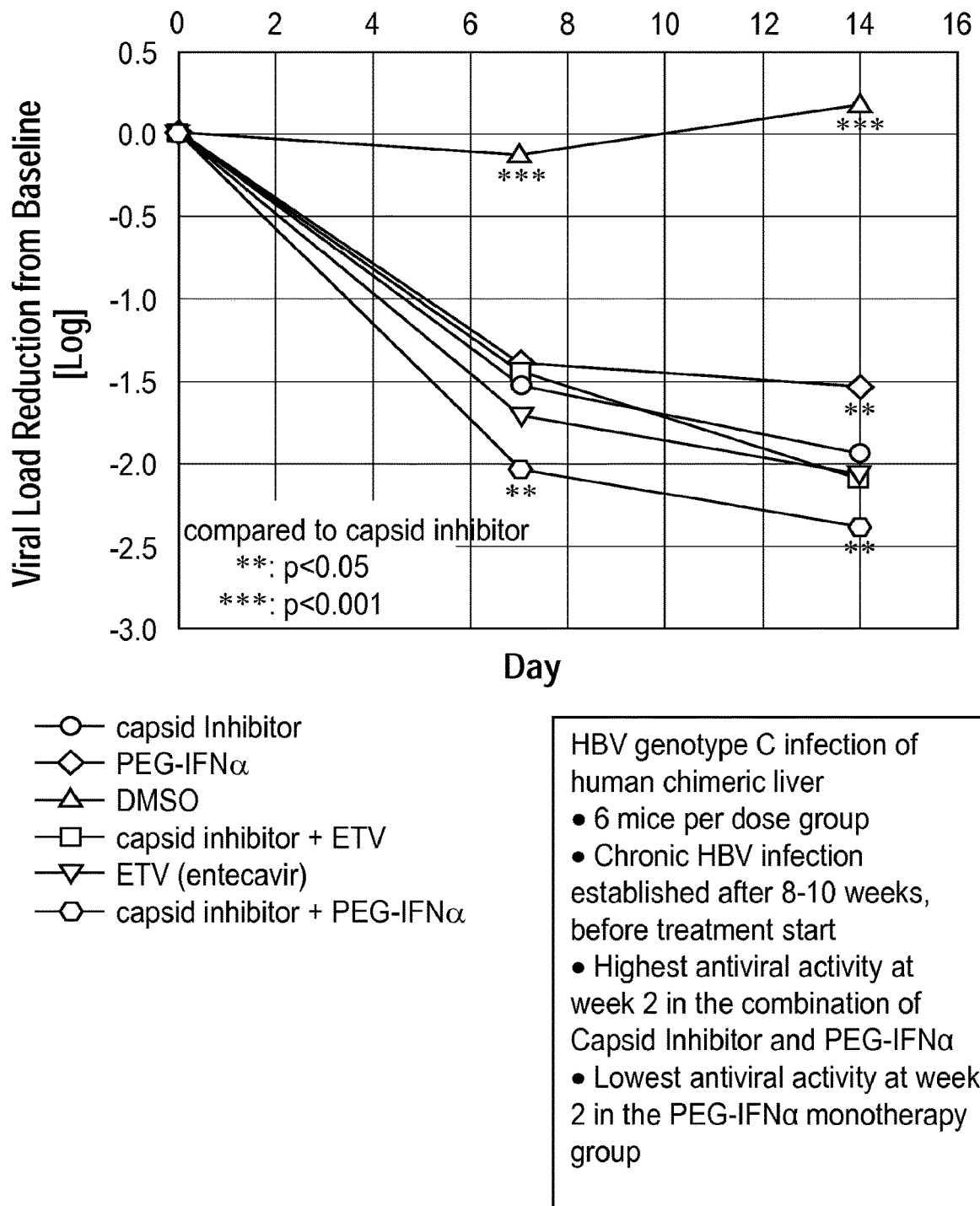
FIG. 1 is a line graph of viral load reduction from baseline ($Log_{10}$; ordinate) as a function of time (days; abscissa) in a uPa-SCID humanized mouse model of HBV infection. Murine subjects were administered amounts of either: capsid inhibitor only; Entecavir (ETV) only; pegylated interferon α (IFN) (PEGASYS) only; a mixture of a capsid inhibitor and Entecavir (capsid inhibitor+ETV); or a mixture of a capsid inhibitor and interferon (capsid inhibitor+PEG-IFNα). Control subjects were administered dimethyl sulfoxide (DMSO) only. N=6

It has been discovered that administering a combination of a compound of Formula I, or a pharmaceutically acceptable salt thereof, and peginterferon alfa-2a (PEGASYS), or another interferon analog, provides surprising, improved effects for treating HBV infection in a subject. Such an approach—combination or co-administration of the two types of agents—can be useful for treating individuals suffering from an HBV infection who do not respond to or are resistant to currently-available therapies. The combination therapy comprising a compound of Formula I and peginterferon alfa-2a, or another interferon analog, provided herein is also useful for improving the efficacy and/or reducing the side effects of currently-available HBV therapies for individuals who do respond to such therapies.

Certain terms used herein are described below. Compounds of the present invention are described using standard nomenclature. Unless defined otherwise, all technical and scientific terms used herein have the same meaning as is commonly understood by one of skill in the art to which this invention belongs.

Combination Therapy

Provided herein is a combination of therapeutic agents and administration methods for the combination of agents to treat HBV infection. As used herein, a "combination of agents" and similar terms refer to a combination of two types of agents: (1) a compound of Formula I, or a pharmaceutically acceptable salt thereof, and (2) and peginterferon alfa-2a or another interferon analog.

Pegylated interferon alpha 2a or peginterferon alfa-2a is a conjugate of poly(ethylene glycol) (PEG) and interferon alpha 2a One brand name for pegylated interferon alpha 2a is PEGASYS. Pegylated interferon alpha 2a compositions and/or methods of making pegylated interferon alpha-2a are disclosed, e.g. in U.S. Pat. Nos. 5,382,657, 5,762,923 and WO 08/145323, all of which are incorporated herein by reference. Pegylated interferon alpha 2a may be prepared using the procedures described in these references.

Compounds of Formula I are useful in the treatment and prevention of HBV in man. In one aspect, the compounds of the invention are useful in HBV treatment by binding to the HBV core protein and thereby disabling all or a subset of the functions HBV core protein plays in HBV replication and persistence such as disrupting, accelerating, reducing delaying and/or inhibiting normal viral capsid assembly and/or disassembly of immature or mature particles, thereby inducing aberrant capsid morphology and leading to antiviral effects such as disruption of virion assembly and/or disassembly and/or virion maturation, and/or virus egress, and/or cccDNA production, maintenance or transcription, and/or modulation of the host innate immune response.

Capsid assembly plays a central role in HBV genome replication. HBV polymerase binds pre-genomic HBV RNA (pgRNA), and pgRNA encapsidation must occur prior to HBV DNA synthesis. Moreover, it is well established that nuclear accumulation of the cccDNA replication intermediate, which is responsible for maintenance of chronic HBV replication in the presence of nucleoside suppressive therapy, requires the capsid for shuttling HBV DNA to the nuclei. Therefore, the HBV core inhibitors or capsid assembly disruptors of the invention have the potential to increase HBV functional cure rates through improved suppression of viral genome replication and through suppression of cccDNA when used alone or in combination with existing HBV drugs such as interferons and nucleos(t)ide inhibitors. The core inhibitors or capsid assembly disruptors of the present invention may also alter normal core protein degradation, potentially leading to altered MHC-1 antigen presentation, which may in turn increase seroconversion/eradication rates through immuno-stimulatory activity, more effectively clearing infected cells. Thus, the compounds of the present invention may have the potential to bind to HBV core protein and alter the function of that protein by interfering with, accelerating, decelerating, disrupting or otherwise modifying the functions associated with HBV core protein.

The compounds useful within the invention may be synthesized using techniques well-known in the art of organic synthesis. The starting materials and intermediates required for the synthesis may be obtained from commercial sources or synthesized according to methods known to those skilled in the art.

In one aspect, the combination therapy comprises a compound of Formula I:

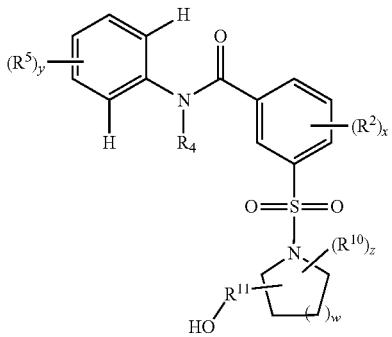

or a pharmaceutically acceptable salt thereof;
wherein
$R^4$ is H or $C_1$-$C_6$ alkyl;
wherein each $R^5$ is independently selected at each occurrence from the group consisting of $CH_3$, $C_1$-$C_6$ alkoxy, halo, —CN, —$NO_2$, -(L)$_m$-$SR^9$, -(L)$_m$-S(=O)$R^9$, -(L)$_m$-S(=O)$_2$$R^9$, -(L)$_m$-NHS(=O)$_2$$R^9$, -(L)$_m$-C(=O)$R^9$, -(L)$_m$-OC(=O)$R^9$, -(L)$_m$$CO_2R^8$, -(L)$_m$-$OCO_2R^8$, -(L)$_m$-N$(R^8)_2$, -(L)$_m$-C(=O)N$(R^8)_2$, -(L)$_m$-OC(=O)N$(R^8)_2$, -(L)$_m$-NHC(=O)NH$(R^8)$, -(L)$_m$-NHC(=O)$R^9$, -(L)$_m$-NHC(=O)$OR^9$, -(L)$_m$-C(OH)$(R^8)_2$, -(L)$_m$C(NH$_2$)$(R^8)_2$, —$C_1$-$C_6$ haloalkyl, —$C_1$-$C_6$ dihaloalkyl and —$C_1$-$C_6$ trihaloalkyl;

L is independently, at each occurrence, a bivalent radical selected from —($C_1$-$C_3$ alkylene)-, —($C_3$-$C_7$ cycloalkylene)-, —($C_1$-$C_3$ alkylene)$_m$-O—($C_1$-$C_3$ alkylene)$_m$-, or —($C_1$-$C_3$ alkylene)$_m$-NH—($C_1$-$C_3$ alkylene)$_m$-;

each $R^8$ is independently, at each occurrence, H, $C_1$-$C_6$ alkyl, —$C_1$-$C_6$ haloalkyl, —$C_1$-$C_6$ dihaloalkyl, —$C_1$-$C_6$ trihaloalkyl, $C_1$-$C_6$ heteroalkyl, $C_3$-$C_{10}$ cycloalkyl, $C_3$-$C_{10}$ heterocycloalkyl, aryl, heteroaryl, —$C_1$-$C_4$ alkyl-($C_3$-$C_{10}$ cycloalkyl), —$C_1$-$C_4$ alkyl-($C_3$-$C_{10}$ heterocycloalkyl), —$C_1$-$C_4$ alkyl-(aryl), or —$C_1$-$C_4$ alkyl(heteroaryl), and wherein the alkyl, heteroalkyl, cycloalkyl, heterocycloalkyl, aryl and heteroaryl is optionally substituted with 1-5 substituents selected from $R^2$;

$R^9$ is, $C_1$-$C_6$ alkyl, —$C_1$-$C_6$ haloalkyl, —$C_1$-$C_6$ dihaloalkyl, —$C_1$-$C_6$ trihaloalkyl, $C_1$-$C_6$ heteroalkyl, $C_3$-$C_{10}$ cycloalkyl, a $C_3$-$C_{10}$ heterocycloalkyl, aryl, heteroaryl, —$C_1$-$C_4$ alkyl-($C_3$-$C_{10}$ cycloalkyl), —$C_1$-$C_4$ alkyl-($C_3$-$C_{10}$ heterocycloalkyl), —$C_1$-$C_4$ alkyl-(aryl), or —$C_1$-$C_4$ alkyl-(heteroaryl), and wherein the alkyl, heteroalkyl, cycloalkyl, heterocycloalkyl, aryl or heteroaryl ring is optionally substituted with 0-5 substituents selected from $R^2$;

$R^{10}$ is OH, $C_1$-$C_6$ alkyl, $C_1$-$C_6$ alkyl-OH, —$C_1$-$C_6$ haloalkyl, —$C_1$-$C_6$ dihaloalkyl, —$C_1$-$C_6$ trihaloalkyl, $C_1$-$C_6$ heteroalkyl, $C_3$-$C_{10}$ cycloalkyl, a $C_3$-$C_{10}$ heterocycloalkyl, aryl, heteroaryl, —$C_1$-$C_4$ alkyl-($C_3$-$C_{10}$ cycloalkyl), —$C_1$-$C_4$ alkyl-($C_3$-$C_{10}$ heterocycloalkyl), —$C_1$-$C_4$ alkyl-(aryl), or —$C_1$-$C_4$ alkyl-(heteroaryl), and wherein the alkyl, heteroalkyl, cycloalkyl, heterocycloalkyl, aryl or heteroaryl ring is optionally substituted with 1-5 substituents selected from $R^2$;

$R^{11}$ is a bond or $C_1$-$C_3$ alkylene, wherein the $C_1$-$C_3$ alkylene is optionally substituted with 1-3 substituents selected from $R^2$;

$R^2$ is independently selected at each occurrence from the group consisting of OH, halo, —CN, —$NO_2$, —$C_1$-$C_6$ alkyl, —$C_1$-$C_6$ alkoxy, —$C_1$-$C_6$ haloalkyl, —$C_1$-$C_6$ dihaloalkyl, —$C_1$-$C_6$ trihaloalkyl, —$C_1$-$C_6$ heteroalkyl, and C(O)—$C_1$-$C_6$ alkyl;

w is 0, 1 or 2;
each occurrence of x is independently selected from the group consisting of 0, 1, 2, 3 and 4;
each occurrence of y is independently selected from the group consisting of 1, 2, and 3;
each occurrence of z is independently selected from the group consisting of 0, 1, 2, and 3;
each occurrence of m is independently 0, 1 or 2.

In one embodiment of Formula I, $R^2$ is independently selected at each occurrence from the group consisting of halo, —CN, —$NO_2$, —$C_1$-$C_6$ alkyl, —$C_1$-$C_6$ alkoxy, —$C_1$-$C_6$ haloalkyl, —$C_1$-$C_6$ dihaloalkyl, —$C_1$-$C_6$ trihaloalkyl, —$C_1$-$C_6$ heteroalkyl, and C(O)—$C_1$-$C_6$ alkyl;

In one embodiment, compounds of Formula I are of the Formula IVa:

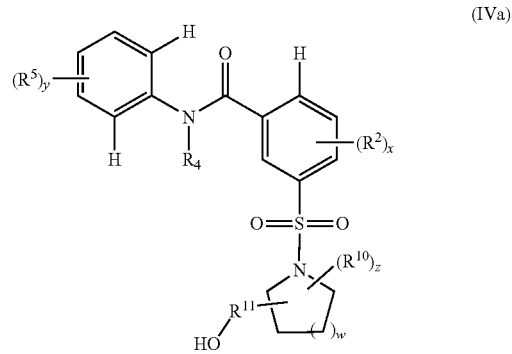

or a pharmaceutically acceptable salt thereof.
In embodiments of Formulae I or IVa,
each $R^5$ is independently selected at each occurrence from the group consisting of $CH_3$, $C_1$-$C_6$ alkoxy, halo, —CN, —$NO_2$, —$C_1$-$C_6$ haloalkyl, —$C_1$-$C_6$ dihaloalkyl, —$C_1$-$C_6$ and trihaloalkyl;

$R^{10}$ is OH, halo, $C_1$-$C_6$ alkyl, $C_1$-$C_6$ alkyl-OH, —$C_1$-$C_6$ chloroalkyl, —$C_1$-$C_6$ dichloroalkyl, —$C_1$-$C_6$ trichloroalkyl, —$C_1$-$C_6$ fluoroalkyl, —$C_1$-$C_6$ difluoroalkyl, —$C_1$-$C_6$ trifluoroalkyl, $C_1$-$C_6$ heteroalkyl, $C_3$-$C_{10}$ cycloalkyl, a $C_3$-$C_{10}$ heterocycloalkyl, aryl, heteroaryl, —$C_1$-$C_4$ alkyl-($C_3$-$C_{10}$ cycloalkyl), —$C_1$-$C_4$ alkyl-($C_3$-$C_{10}$ heterocycloalkyl), —$C_1$-$C_4$ alkyl-(aryl), or —$C_1$-$C_4$ alkyl-(heteroaryl), and wherein the alkyl, heteroalkyl, cycloalkyl, heterocycloalkyl, aryl or heteroaryl ring is optionally substituted with 1-5 substituents selected from $R^2$;

$R^{11}$ is a bond or $C_1$-$C_3$ alkylene, wherein the $C_1$-$C_3$ alkylene is optionally substituted with 1-3 substituents selected from $R^2$;

$R^2$ is independently selected at each occurrence from the group consisting of halo, —CN, —$NO_2$, —$C_1$-$C_6$ alkyl, —$C_1$-$C_6$ alkoxy, —$C_1$-$C_6$ fluoroalkyl, —$C_1$-$C_6$ heteroalkyl, C(O)—$C_1$-$C_6$ alkyl, and C(O)—$C_1$-$C_6$ alkoxy.

In other embodiments of Formulae I or IVa, each $R^5$ is independently selected at each occurrence from the group consisting of $CH_3$, $C_1$-$C_6$ alkoxy, halo, fluoromethyl, difluoromethyl, trifluoromethyl, chloromethyl, dichloromethyl, and trichloromethyl;

$R^{10}$ is OH, halo, $C_1$-$C_6$ alkyl, $C_1$-$C_6$ alkyl-OH, $C_1$-$C_6$ fluoroalkyl, $C_1$-$C_6$ difluoroalkyl, $C_1$-$C_6$ trifluoroalkyl, $C_1$-$C_6$ heteroalkyl, $C_3$-$C_{10}$ cycloalkyl, $C_3$-$C_{10}$ heterocycloalkyl, aryl, heteroaryl, —$C_1$-$C_4$ alkyl-($C_3$-$C_{10}$ cycloalkyl), alkyl-($C_3$-$C_{10}$ heterocycloalkyl), —$C_1$-$C_4$ alkyl-(aryl), or —$C_1$-$C_4$ alkyl-(heteroaryl), and wherein the alkyl, heteroalkyl, cycloalkyl, heterocycloalkyl, aryl or heteroaryl ring is optionally substituted with 1-5 substituents selected from $R^2$;

$R^{11}$ is a bond or $C_1$-$C_3$ alkylene;

$R^2$ is independently selected at each occurrence from the group consisting of halo, —CN, —$NO_2$, —$C_1$-$C_6$ alkyl, —$C_1$-$C_6$ alkoxy, —$C_1$-$C_6$ fluoroalkyl, —$C_1$-$C_6$ heteroalkyl, and C(O)—$C_1$-$C_6$ alkyl, and C(O)—$C_1$-$C_6$ alkoxy.

In other embodiments of Formulae I and IVa, $R^5$ (i.e., $(R^5)_y$) is 3-F, 3-Cl, 3-$CH_3$, 3-$CH_2F$, 3-$CHF_2$, 4-F, 3-$CH_3$-4-F, 3-Cl-4-F, 3-Br-4-F, 3,4,5-trifluoro, 3,4,5-trichloro, or 3-chloro-4,5-difluoro. In another embodiment, w is 1 or 2.

In yet other embodiments of Formulae I and IVa, $R^{11}$ is a bond or $C_1$-$C_3$ alkylene;

$R^{10}$ is OH, halo, $C_1$-$C_6$ alkyl, $C_1$-$C_6$ alkyl-OH, —$C_1$-$C_6$ chloroalkyl, —$C_1$-$C_6$ dichloroalkyl, —$C_1$-$C_6$ trichloroalkyl, —$C_1$-$C_6$ fluoroalkyl, —$C_1$-$C_6$ difluoroalkyl, —$C_1$-$C_6$ trifluoroalkyl, $C_3$-$C_{10}$ cycloalkyl, $C_3$-$C_{10}$ heterocycloalkyl, or phenyl, wherein the $C_3$-$C_{10}$ cycloalkyl, a $C_3$-$C_{10}$ heterocycloalkyl, or phenyl groups are optionally substituted with 1-5 substituents selected from halo, —$C_1$-$C_6$ alkyl, and —$C_1$-$C_6$ alkoxy; and z is 0 or 1.

In another embodiment, compounds of Formula I are of the Formula IVb:

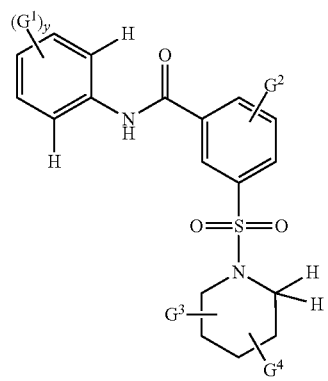

(IVb)

or pharmaceutically acceptable salts thereof;

wherein $G^1$ is independently selected at each occurrence from $CH_3$, $OCH_3$, halo, $CF_3$, $CCl_3$, $CH_2Cl$, $CCl_2H$, $CF_2H$, $CH_2F$, and $CF_3$;

$G^2$ is H, $C_1$-$C_4$ alkyl, or halo;

$G^3$ is OH, $CH_2OH$, or $CH_2CH_2OH$;

$G^4$ is H, OH, halo, $C_1$-$C_6$ alkyl, $C_1$-$C_6$ alkyl-OH, —$C_1$-$C_6$ chloroalkyl, —$C_1$-$C_6$ dichloroalkyl, —$C_1$-$C_6$ trichloroalkyl, —$C_1$-$C_6$ fluoroalkyl, —$C_1$-$C_6$ difluoroalkyl, —$C_1$-$C_6$ trifluoroalkyl, or phenyl, wherein the phenyl group is optionally independently substituted with 1-5 substituents selected from halo, —$C_1$-$C_6$ alkyl, and —$C_1$-$C_6$ alkoxy; and y is 1, 2, or 3.

In an embodiment of Formula IVb, $G^1$ is independently selected at each occurrence from halo, $CF_3$, $CCl_3$, $CH_2Cl$, $CCl_2H$, $CF_2H$, $CH_2F$, and $CF_3$.

In another embodiment, compounds of Formula I are of the Formula IVc:

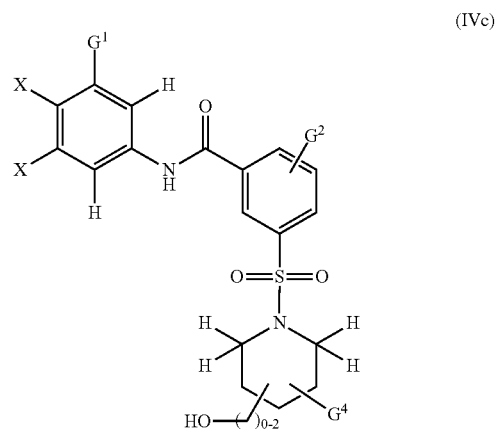

(IVc)

or pharmaceutically acceptable salts thereof;

wherein X is halo;

$G^1$ is hydrogen or halo;

$G^2$ is H, $C_1$-$C_4$ alkyl, or halo; and $G^4$ is H, halo, $C_1$-$C_4$ alkyl, or OH.

In one embodiment of Formula IVc, $G^2$ is $C_1$-$C_4$ alkyl or halo, and wherein $G^2$ is in the 2, 3, or 4 position of the phenyl ring.

In a particular embodiment, the compound of Formula I is a compound provided in the following table, or a pharmaceutically acceptable salt thereof:

| Structure MS(M + H)+ | Cmp. ID |
|---|---|
| ![compound structure] | 960_D1 |
| 451 | |

| Structure MS(M + H)+ | Cmp. ID |
|---|---|
| 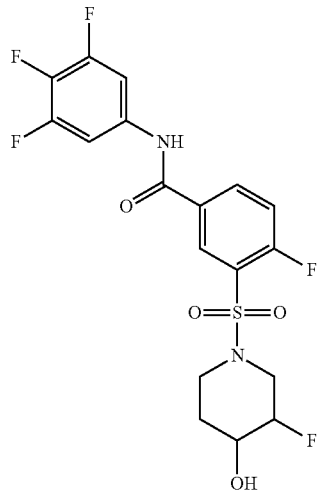 451 | 960_D2 |
| 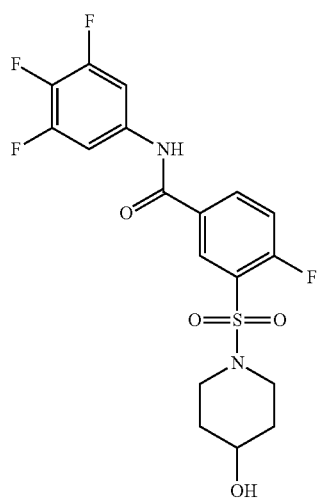 433 | 890 |
| Structure MS(M + H)+ | Cmp. ID |
|---|---|
| 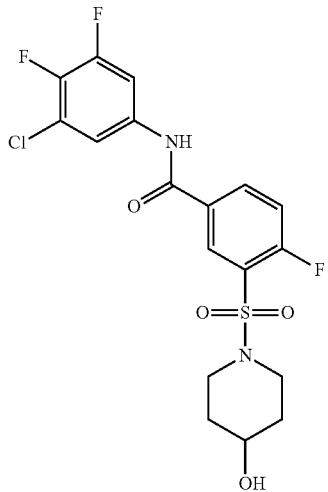 449/451 | 893 |
| 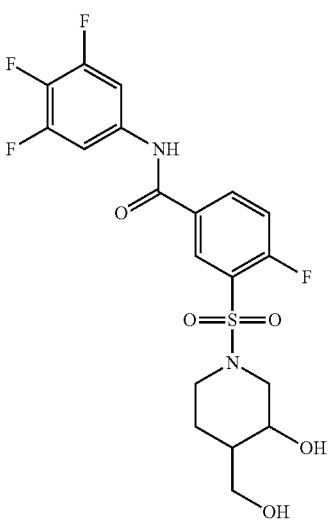 [SMILES: O=C(Nc1cc(F)c(F)c(F)c1)c1ccc(F)c(S(=O)(=O)N2CCC(CO)C(O)C2)c1] 463 | 946_D1 |

-continued
| Structure MS(M + H)+ | Cmp. ID |
|---|---|
| 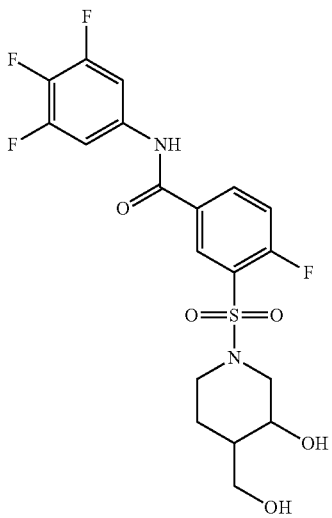 | 946_D2 |
| 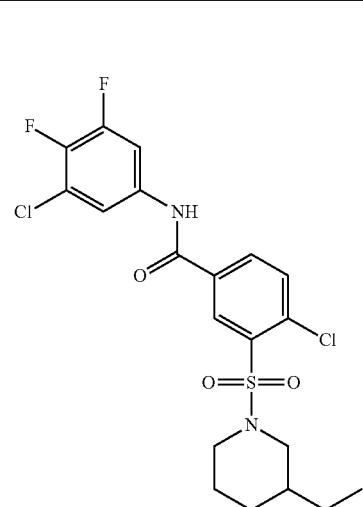 429 | 925 |
| 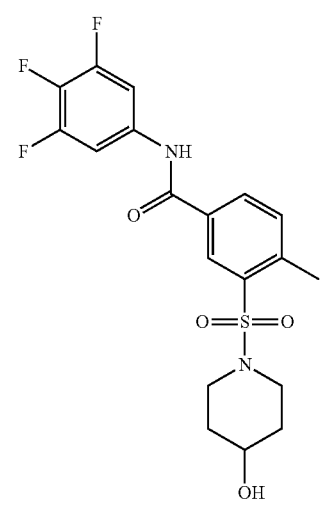 479/481 | 1080 |
-continued
| Structure MS(M + H)+ | Cmp. ID |
|---|---|
|  493/495 | 1084_D1 |
| 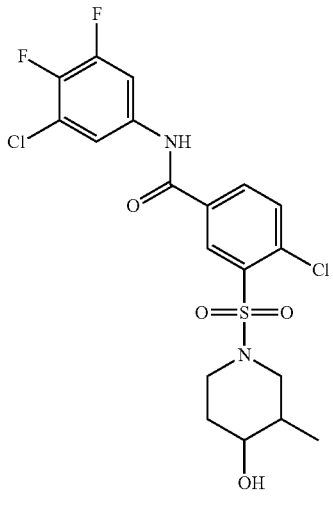 493/495 | 1084_D2 |

| Structure MS(M + H)+ | Cmp. ID |
|---|---|
| 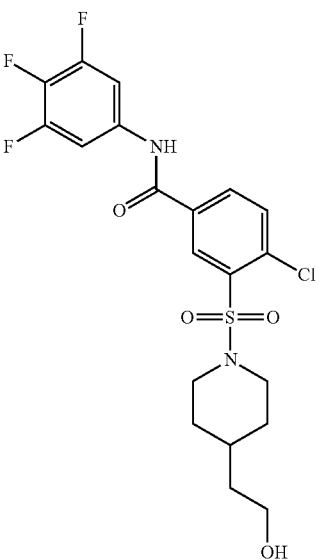 477/479 | 1085 |
| 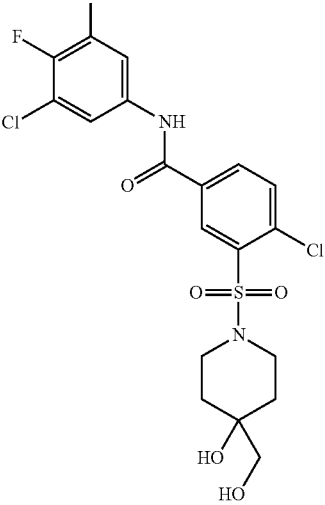 493/495 | 1088 |
| Structure MS(M + H)+ | Cmp. ID |
|---|---|
| 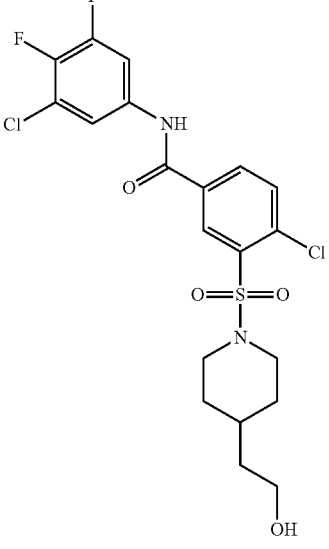 495/497 | 1100 |
| 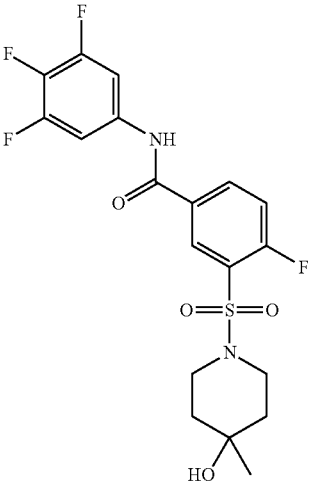 447 | 1161 |

| Structure MS(M + H)+ | Cmp. ID |
|---|---|
| 3,4,5-trifluorophenyl-NH-C(O)-[benzene with F]-SO2-N(piperidine-4-OH, 4-CH2OH); 463 | 916 |
| 3,4,5-trifluorophenyl-NH-C(O)-[benzene with Cl]-SO2-N(piperidine-4-OH); 449/451 | 1057 |

| Structure MS(M + H)+ | Cmp. ID |
|---|---|
| 3-chloro-4,5-difluorophenyl-NH-C(O)-[benzene with Cl]-SO2-N(piperidine-4-OH); 465/467 | 1060 |
| 3,4,5-trifluorophenyl-NH-C(O)-[benzene with Cl]-SO2-N(3-ethyl-piperidine-4-OH); 477/479 | 1081_D1 |

-continued

| Structure MS(M + H)⁺ | Cmp. ID |
|---|---|
| (structure) 477/479 | 1081_D2 |
| (structure) 479/481 | 1130 |

-continued

| Structure MS(M + H)⁺ | Cmp. ID |
|---|---|
| (structure) 467/469 | 1135_D1 |
| (structure) 467/469 | 1135_D2 |

| Structure MS(M + H)+ | Cmp. ID |
|---|---|
| 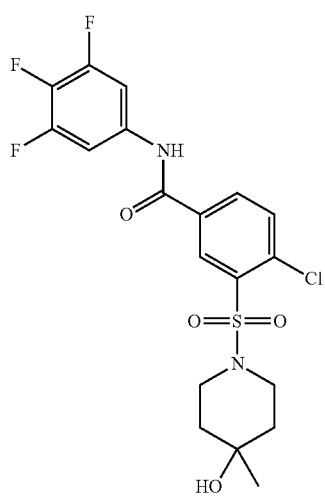 463/465 | 1073 |
| 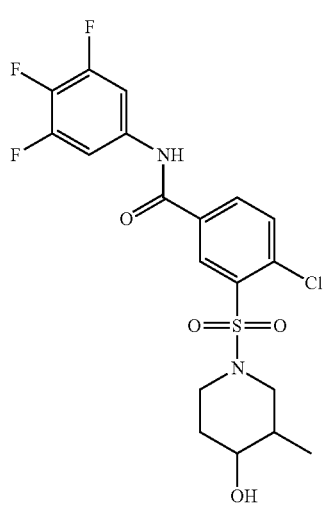 463/465 | 1077_D1 |

| Structure MS(M + H)+ | Cmp. ID |
|---|---|
| 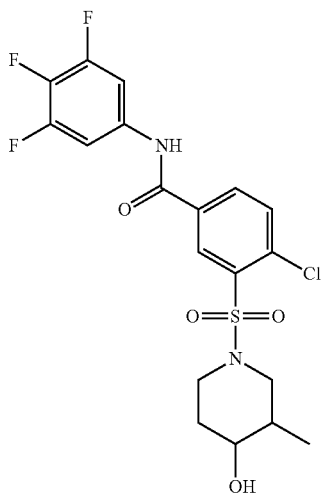 463/465 | 1077_D2 |
| 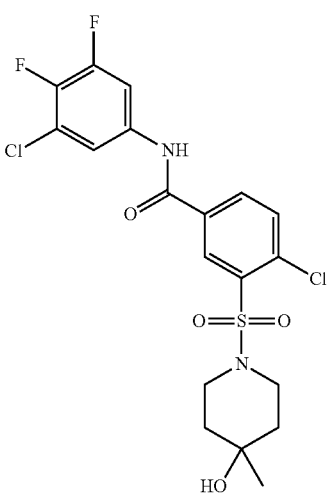 461/463 | 1076 |

Examples of compounds of Formula I include the compounds described in U.S. Pat. No. 8,629,274, which is incorporated herein by reference in its entirety. Methods of making compounds of Formula I, including the compounds of the above table, can be found in U.S. Pat. No. 8,629,274.

Compounds of Formula I may be prepared by the reaction sequence that is illustrated in Scheme 1.

Scheme 1.

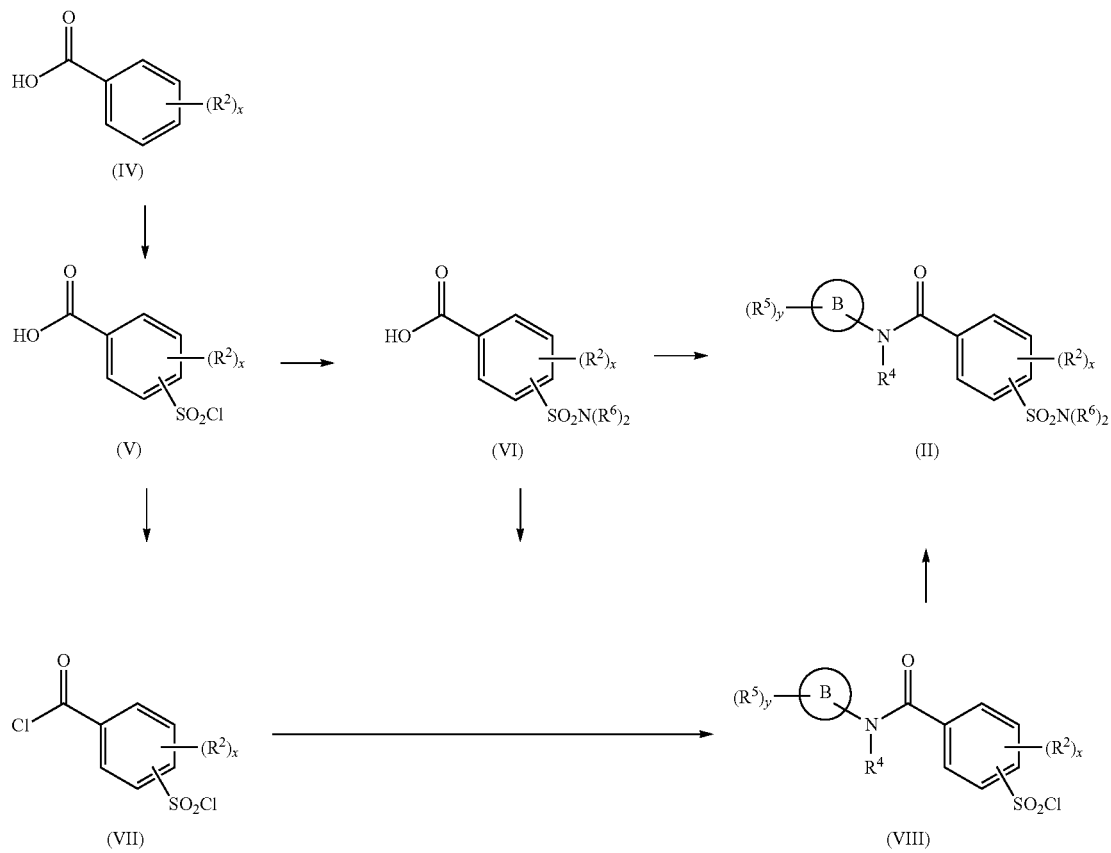

The compound of Formula (IV) from Scheme 1 may be reacted with chlorosulfonic acid to yield the sulfonyl chloride of formula (V). The compound of Formula (V) may be reacted with a secondary or primary amine of formula $HNR^6R^6$, in a solvent such as but not limited to tetrahydrofuran, dichloromethane, ethyl ether or a mixture thereof, preferably in the presence of a tertiary base such as but not limited to triethylamine, diisopropylethylamine or pyridine, to yield the compound of Formula (VI), which may be coupled to an amine via an amide bond, yielding the compound of Formula (II). The amide coupling may be performed in the presence of a coupling agent, such as but not limited to DCC (N,N'-dicyclohexyl carbodiimide), DIC (N,N'-diisopropylcarbodiimide), EDC (1-ethyl-3-(3-dimethylaminopropyl) carbodiimide), HBTU (O-benzotriazole-N,N,N',N'-tetramethyl-uronium-hexafluoro-phosphate), HATU (2-(1H-7-azabenzotriazol-1-yl)-1,1,3,3-tetramethyl uronium hexafluorophosphate methanaminium), HCTU ((2-(6-chloro-1H-benzotriazole-1-yl)-1,1,3,3-tetramethylaminium hexafluorophosphate), TBTU (O-(benzotriazol-1-yl)-N,N,N',N'-tetramethyluronium tetrafluoroborate), or PyBOP (benzotriazol-1-yl-oxytripyrrolidino-phosphonium hexafluorophosphate), in a solvent such as but not limited to tetrahydrofuran, dichloromethane, or a mixture thereof, and in the optional presence of a tertiary base, such as but not limited to triethylamine, diisopropylethylamine or pyridine. Alternatively, the sulfonyl chloride of Formula (V) may be reacted with a chlorinating reagent, such as but not limited to thionyl chloride, phosgene, diphosgene or triphosgene, to yield the acyl chloride of Formula (VII). The compound of Formula (VII) may then be reacted with an amine in a solvent such as but not limited to tetrahydrofuran, dichloromethane, ethyl ether or a mixture thereof, under conditions that do not promote the reaction of the sulfonyl chloride group with the amine, to yield the compound of Formula (VIII), which may then be reacted with the amine $HNR^6R^6$ in a solvent such as but not limited to tetrahydrofuran, toluene, dichloromethane, or a mixture thereof, and in the presence of a tertiary base, such as but not limited to triethylamine, diisopropylethylamine or pyridine, to yield the compound of Formula (II).

As used herein, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl and isobutyl.

As used herein, the term "$C_{3-6}$ cycloalkyl" refers to saturated or unsaturated monocyclic or bicyclic hydrocarbon groups of 3-6 carbon atoms, preferably 5 carbon atoms. Exemplary monocyclic hydrocarbon groups include, but are not limited to, cyclopropyl, cyclobutyl, and cyclopentyl.

The term "halogen" or "halo" refers to chloro, bromo, fluoro, and iodo groups.

Agents may contain one or more asymmetric elements such as stereogenic centers or stereogenic axes, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms; all isomeric forms of the compounds are included in the present invention. In these situations, the single enantiomers (optically active forms) can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

Unless otherwise specified, or clearly indicated by the text, reference to compounds useful in the combination therapy of the invention includes both the free base of the compounds, and all pharmaceutically acceptable salts of the compounds.

As used herein, the term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17.sup.th ed., Mack Publishing Company, Easton, Pa., 1985, p. 1418 and Journal of Pharmaceutical Science, 66, 2 (1977), each of which is incorporated herein by reference in its entirety.

Provided herein is a combination therapy comprising a compound of Formula I, or a pharmaceutically acceptable salt thereof, and PEGASYS. Administration of the combination includes administration of the combination in a single formulation or unit dosage form, administration of the individual agents of the combination concurrently but separately, or administration of the individual agents of the combination sequentially by any suitable route. The dosage of the individual agents of the combination may require more frequent administration of one of the agent(s) as compared to the other agent(s) in the combination. Therefore, to permit appropriate dosing, packaged pharmaceutical products may contain one or more dosage forms that contain the combination of agents, and one or more dosage forms that contain one of the combination of agents, but not the other agent(s) of the combination.

The term "single formulation" as used herein refers to a single carrier or vehicle formulated to deliver effective amounts of both therapeutic agents to a patient. The single vehicle is designed to deliver an effective amount of each of the agents, along with any pharmaceutically acceptable carriers or excipients. In some embodiments, the vehicle is a tablet, capsule, pill, or a patch. In other embodiments, the vehicle is a solution or a suspension.

The term "unit dose" is used herein to mean simultaneous administration of both agents together, in one dosage form, to the patient being treated. In some embodiments, the unit dose is a single formulation. In certain embodiments, the unit dose includes one or more vehicles such that each vehicle includes an effective amount of at least one of the agents along with pharmaceutically acceptable carriers and excipients. In some embodiments, the unit dose is one or more tablets, capsules, pills, or patches administered to the patient at the same time.

The term "treat" is used herein to mean to relieve, reduce or alleviate, at least one symptom of a disease in a subject. Within the meaning of the present invention, the term "treat" also denotes, to arrest, delay the onset (i.e., the period prior to clinical manifestation of a disease or symptom of a disease) and/or reduce the risk of developing or worsening a symptom of a disease.

The term "subject" is intended to include animals. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from an HBV infection.

The term "about" or "approximately" usually means within 20%, more preferably within 10%, and most preferably still within 5% of a given value or range. Alternatively, especially in biological systems, the term "about" means within about a log (i.e., an order of magnitude) preferably within a factor of two of a given value.

The terms "capsid assembly inhibitor," "capsid inhibitor," "capsid assembly disruptor," and "core inhibitor" refer to the same mode of action. Without being limited by any theoretical explanation, this mode of action may be initiated by binding of compounds of the invention to HBV core protein and altering the function of that protein by interfering with, accelerating, decelerating, disrupting or otherwise modifying the functions associated with HBV core protein.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, or in separate containers (e.g., capsules) for each active ingredient. In addition, such administration also encompasses use of each type of therapeutic agent in a sequential manner, either at approximately the same time or at different times. In either case, the treatment regimen will provide beneficial effects of the drug combination in treating the conditions or disorders described herein.

The combination of agents described herein provide improved HBV suppression or HBV cure efficacy compared to the respective monotherapies. In certain embodiments, the combination of agents described herein display a synergistic effect. The term "synergistic effect" as used herein, refers to action of two agents such as, for example, a compound of Formula I, or a pharmaceutically acceptable salt thereof, and Pegasys, producing an effect, for example, slowing the symptomatic progression of cancer or symptoms thereof, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

In an embodiment, provided herein is a combination therapy comprising an effective amount of a compound of Formula I, or a pharmaceutically acceptable salt thereof, and PEGASYS. An "effective amount" of a combination of agents is an amount sufficient to provide an observable improvement over the baseline clinically observable signs and symptoms of the disorders treated with the combination.

An "oral dosage form" includes a unit dosage form prescribed or intended for oral administration.

Methods of Treatment

In one aspect of the invention, provided herein is a method of treating an HBV infection in a subject in need thereof, comprising administering to the subject a capsid assembly inhibitor and an interferon.

In one embodiment, the interferon is selected from the group consisting of interferon alpha, interferon alpha-2a, recombinant interferon alpha-2a, peginterferon-alpha 2a, interferon alpha-2b, recombinant interferon alpha-2b, interferon alpha-2b XL, peginterferon alpha-2b, glycosylated interferon alpha-2b, interferon alpha-2c, recombinant interferon alpha-2c, interferon beta, interferon beta-1a, peginterferon beta-1a, interferon delta, interferon lambda, peginterferon lambda-1, interferon omega, interferon tau, gamma interferon, interferon alfacon-1, interferon alpha-n1, interferon alpha-n3, albinterferon alpha-2b, BLX-883, DA-3021, PEG-Infergen, and BELEROFON. In a particular embodiment, the interferon is selected from the group consisting of peginterferon alpha-2a, peginterferon alpha-2b, glycosylated interferon alpha-2b, peginterferon beta-1a, and peginterferon lambda-1. In a specific embodiment, the interferon is peginterferon alpha-2a.

In still another embodiment, the capsid assembly inhibitor is a compound of Formula (I).

The invention includes a method of treatment of an HBV infection in an individual in need thereof, comprising administering to the individual the combination therapy of the invention (i.e., a compound of Formula I in combination with peginterferon alfa-2a).

The invention also includes a method of reducing viral load associated with an HBV infection in an individual in need thereof, comprising administering to the individual the combination therapy of the invention.

The invention further includes a method of reducing reoccurrence of an HBV infection in an individual in need thereof, comprising administering to the individual the combination therapy of the invention.

The invention also includes a method of reducing the physiological impact of an HBV infection in an individual in need thereof, comprising administering to the individual the combination therapy of the invention.

The invention further includes a method of reducing, slowing, or inhibiting an HBV infection in an individual in need thereof, comprising administering to the individual the combination therapy of the invention.

The invention also includes a method of inducing remission of hepatic injury from an HBV infection in an individual in need thereof, comprising administering to the individual the combination therapy of the invention.

The invention further includes a method of reducing the physiological impact of long-term antiviral therapy for HBV infection in an individual in need thereof, comprising administering to the individual the combination therapy of the invention.

The invention also includes a method of eradicating an HBV infection in an individual in need thereof, comprising administering to the individual the combination therapy of the invention.

The invention further includes a method of prophylactically treating an HBV infection in an individual in need thereof, wherein the individual is afflicted with a latent HBV infection, comprising administering to the individual the combination therapy of the invention.

In one embodiment, the individual is refractory or non-responsive to other therapeutic classes of HBV drugs (e.g., HBV polymerase inhibitors, interferons, viral entry inhibitors, viral maturation inhibitors, literature-described capsid assembly modulators, antiviral compounds of distinct or unknown mechanism, and the like, or combinations thereof). In another embodiment, the method of the invention reduces viral load in an individual suffering from an HBV infection to a greater extent compared to the extent that other therapeutic classes of HBV drugs reduce viral load in the individual.

In one embodiment, the method of the invention reduces viral load in an individual suffering from an HBV infection, thus allowing lower doses or varying regimens of combination therapies to be used.

In one embodiment, the method of the invention causes a lower incidence of viral mutation and/or viral resistance compared to other classes of HBV drugs, thereby allowing for long term therapy and minimizing the need for changes in treatment regimens.

In one embodiment, the method of the invention increases the seroconversion rate beyond that of current treatment regimens.

In one embodiment, the method of the invention increases and/or normalizes and/or restores normal health, elicits full recovery of normal health, restores life expectancy, and/or resolves the viral infection in the individual in need thereof.

In one embodiment, the method of the invention eradicates HBV from an individual infected with HBV, thereby obviating the need for long term and/or life-long treatment, or shortening the duration of treatment, and/or allowing for reduction in dosing of other antiviral agents.

Accordingly, in one embodiment, provided herein is a method of treating an HBV infection in an individual in need thereof, comprising administering to the individual a therapeutically effective amount of a compound of Formula I, or a pharmaceutically acceptable salt thereof, and PEGASYS.

In another embodiment, provided herein is a method of treating an HBV infection in an individual in need thereof, comprising administering to the individual a therapeutically effective amount of a compound of Formula IVa, or a pharmaceutically acceptable salt thereof, and PEGASYS.

In another embodiment, provided herein is a method of treating an HBV infection in an individual in need thereof, comprising administering to the individual a therapeutically effective amount of a compound of Formula IVb, or a pharmaceutically acceptable salt thereof, and PEGASYS.

In another embodiment, provided herein is a method of treating an HBV infection in an individual in need thereof, comprising administering to the individual a therapeutically effective amount of a compound of Formula IVc, or a pharmaceutically acceptable salt thereof, and PEGASYS.

In another embodiment, provided herein is a method of treating an HBV infection in an individual in need thereof, comprising administering to the individual a therapeutically effective amount of compound 960, or a pharmaceutically acceptable salt thereof, and PEGASYS.

In another embodiment, provided herein is a method of treating an HBV infection in an individual in need thereof, comprising administering to the individual a therapeutically effective amount of compound 890, or a pharmaceutically acceptable salt thereof, and PEGASYS.

In another embodiment, provided herein is a method of treating an HBV infection in an individual in need thereof, comprising administering to the individual a therapeutically effective amount of compound 893, or a pharmaceutically acceptable salt thereof, and PEGASYS.

In another embodiment, provided herein is a method of treating an HBV infection in an individual in need thereof, comprising administering to the individual a therapeutically effective amount of compound 946, or a pharmaceutically acceptable salt thereof, and PEGASYS.

In another embodiment, provided herein is a method of treating an HBV infection in an individual in need thereof, comprising administering to the individual a therapeutically effective amount of compound 925, or a pharmaceutically acceptable salt thereof, and PEGASYS.

In another embodiment, provided herein is a method of treating an HBV infection in an individual in need thereof, comprising administering to the individual a therapeutically effective amount of compound 1080, or a pharmaceutically acceptable salt thereof, and PEGASYS.

In another embodiment, provided herein is a method of treating an HBV infection in an individual in need thereof, comprising administering to the individual a therapeutically effective amount of compound 1084, or a pharmaceutically acceptable salt thereof, and PEGASYS.

In another embodiment, provided herein is a method of treating an HBV infection in an individual in need thereof, comprising administering to the individual a therapeutically effective amount of compound 1085, or a pharmaceutically acceptable salt thereof, and PEGASYS.

In another embodiment, provided herein is a method of treating an HBV infection in an individual in need thereof, comprising administering to the individual a therapeutically effective amount of compound 1088, or a pharmaceutically acceptable salt thereof, and PEGASYS.

In another embodiment, provided herein is a method of treating an HBV infection in an individual in need thereof, comprising administering to the individual a therapeutically effective amount of compound 1100, or a pharmaceutically acceptable salt thereof, and PEGASYS.

In another embodiment, provided herein is a method of treating an HBV infection in an individual in need thereof, comprising administering to the individual a therapeutically effective amount of compound 1161, or a pharmaceutically acceptable salt thereof, and PEGASYS.

In another embodiment, provided herein is a method of treating an HBV infection in an individual in need thereof, comprising administering to the individual a therapeutically effective amount of compound 916, or a pharmaceutically acceptable salt thereof, and PEGASYS.

In another embodiment, provided herein is a method of treating an HBV infection in an individual in need thereof, comprising administering to the individual a therapeutically effective amount of compound 1057, or a pharmaceutically acceptable salt thereof, and PEGASYS.

In another embodiment, provided herein is a method of treating an HBV infection in an individual in need thereof, comprising administering to the individual a therapeutically effective amount of compound 1060, or a pharmaceutically acceptable salt thereof, and PEGASYS.

In another embodiment, provided herein is a method of treating an HBV infection in an individual in need thereof, comprising administering to the individual a therapeutically effective amount of compound 1081, or a pharmaceutically acceptable salt thereof, and PEGASYS.

In another embodiment, provided herein is a method of treating an HBV infection in an individual in need thereof, comprising administering to the individual a therapeutically effective amount of compound 1130, or a pharmaceutically acceptable salt thereof, and PEGASYS.

In another embodiment, provided herein is a method of treating an HBV infection in an individual in need thereof, comprising administering to the individual a therapeutically effective amount of compound 1135, or a pharmaceutically acceptable salt thereof, and PEGASYS.

In another embodiment, provided herein is a method of treating an HBV infection in an individual in need thereof, comprising administering to the individual a therapeutically effective amount of compound 1073, or a pharmaceutically acceptable salt thereof, and PEGASYS.

In another embodiment, provided herein is a method of treating an HBV infection in an individual in need thereof, comprising administering to the individual a therapeutically effective amount of compound 1077, or a pharmaceutically acceptable salt thereof, and PEGASYS.

In another embodiment, provided herein is a method of treating an HBV infection in an individual in need thereof, comprising administering to the individual a therapeutically effective amount of compound 1076, or a pharmaceutically acceptable salt thereof, and PEGASYS.

Dosages

The optimal dose of the combination of agents for treatment of disease can be determined empirically for each individual using known methods and will depend upon a variety of factors, including, though not limited to, the degree of advancement of the disease; the age, body weight, general health, gender and diet of the individual; the time and route of administration; and other medications the individual is taking. Optimal dosages may be established using routine testing and procedures that are well known in the art.

The amount of combination of agents that may be combined with the carrier materials to produce a single dosage form will vary depending upon the individual treated and the particular mode of administration. In some embodiments the unit dosage forms containing the combination of agents as described herein will contain the amounts of each agent of the combination that are typically administered when the agents are administered alone.

In an embodiment of the combination provided herein, each agent is administered at dosages that would not be effective when one or both of the agents are administered alone, but which amounts are effective in combination. For example, in an embodiment, peginterferon alfa-2a and a compound of Formula I are administered at dosages that would not be effective when one or both of the peginterferon alfa-2a and compound of Formula I are administered alone, but which amounts are effective in combination.

Frequency of dosage may vary depending on the compound used and the particular condition to be treated or prevented. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

In an embodiment of the combination provided herein, one or more agents are administered for a duration that is shorter compared to the duration when either of the agents are administered alone. For example, current treatment guidelines recommend interferon treatment for 12 months. In an embodiment of the combination provided herein (e.g., a compound of Formula I and interferon), the duration of interferon treatment is 12 months or less, e.g., 11 months or less, e.g., 10 months or less, e.g., 9 months or less, e.g., 8 months or less, e.g., 7 months or less, e.g., 6 months or less, e.g., 5 months or less, e.g., 4 months or less, e.g., 3 months or less, e.g., 2 months or less, e.g., 1 month or less. In another embodiment, a treatment of peginterferon alfa-2a and a compound of Formula I are administered for 12 months or less, e.g., 11 months or less, e.g., 10 months or less, e.g., 9 months or less, e.g., 8 months or less, e.g., 7 months or less, e.g., 6 months or less, e.g., 5 months or less, e.g., 4 months or less, e.g., 3 months or less, e.g., 2 months or less, e.g., 1 month or less.

The dosage form can be prepared by various conventional mixing, comminution and fabrication techniques readily apparent to those skilled in the chemistry of drug formulations.

The oral dosage form containing the combination of agents or individual agents of the combination of agents may be in the form of micro-tablets enclosed inside a capsule, e.g., a gelatin capsule. For this, a gelatin capsule as is employed in pharmaceutical formulations can be used, such as the hard gelatin capsule known as CAPSUGEL, available from Pfizer.

Many of the oral dosage forms useful herein contain the combination of agents or individual agents of the combination of agents in the form of particles. Such particles may be compressed into a tablet, present in a core element of a coated dosage form, such as a taste-masked dosage form, a press coated dosage form, or an enteric coated dosage form, or may be contained in a capsule, osmotic pump dosage form, or other dosage form.

The drug compounds of the present invention are present in the combinations, dosage forms, pharmaceutical compositions and pharmaceutical formulations disclosed herein in a ratio in the range of 100:1 to 1:100. For example, the ratio of a compound of Formula I: peginterferon alfa-2a (or another interferon analog) can be in the range of 1:100 to 1:1, for example, 1:100, 1:90, 1:80, 1:70, 1:60, 1:50, 1:40, 1:30, 1:20, 1:10, 1:5, 1:2, or 1:1 of Formula I: peginterferon alfa-2a. In another example, the ratio of peginterferon alfa-2a: a compound of Formula I can be in the range of 1:100 to 1:1, for example, 1:100, 1:90, 1:80, 1:70, 1:60, 1:50, 1:40, 1:30, 1:20, 1:10, 1:5, 1:2, or 1:1 of peginterferon alfa-2a: a compound of Formula I.

The optimum ratios, individual and combined dosages, and concentrations of the drug compounds that yield efficacy without toxicity are based on the kinetics of the active ingredients' availability to target sites, and are determined using methods known to those of skill in the art.

The pharmaceutical compositions or combinations provided herein can be tested in clinical studies. Suitable clinical studies may be, for example, open label, dose escalation studies in patients with proliferative diseases. Such studies prove in particular the improvement of efficacy of the active ingredients of the combination of the invention. The beneficial effects on proliferative diseases may be determined directly through the results of these studies which are known as such to a person skilled in the art. Such studies may be, in particular, suitable to compare the effects of a monotherapy using the active ingredients and a combination of the invention.

The administration of a combination therapy of the invention may result not only in a beneficial effect, e.g. an improved therapeutic effect, e.g. with regard to alleviating, delaying progression of or inhibiting the symptoms, but also in further surprising beneficial effects, e.g. fewer side-effects, an improved quality of life or a decreased morbidity, compared with a monotherapy applying only one of the pharmaceutically active ingredients used in the combination of the invention.

A further benefit may be that lower doses of the active ingredients of the combination of the invention may be used, for example, that the dosages need not only often be smaller but may also be applied less frequently, which may diminish the incidence or severity of side-effects. This is in accordance with the desires and requirements of the patients to be treated.

It is one objective of this invention to provide a pharmaceutical composition comprising a quantity, which may be jointly therapeutically effective at targeting or preventing HBV infection. In this composition, a compound of Formula I and peginterferon alfa-2a (or another interferon analog) may be administered together, one after the other or separately in one combined unit dosage form or in two separate unit dosage forms. The unit dosage form may also be a fixed combination.

The pharmaceutical compositions for separate administration of both compounds, or for the administration in a fixed combination, i.e. a single galenical composition comprising both compounds according to the invention may be prepared in a manner known per se and are those suitable for enteral, such as oral or rectal, and parenteral administration to mammals (warm-blooded animals), including humans, comprising a therapeutically effective amount of at least one pharmacologically active combination partner alone, e.g. as indicated above, or in combination with one or more pharmaceutically acceptable carriers or diluents, especially suitable for enteral or parenteral application.

Formulations

The drug combinations provided herein may be formulated by a variety of methods apparent to those of skill in the art of pharmaceutical formulation. The various release properties described above may be achieved in a variety of different ways. Suitable formulations include, for example, tablets, capsules, press coat formulations, and other easily administered formulations.

Suitable pharmaceutical formulations may contain, for example, from about 0.1% to about 99.9%, preferably from about 1% to about 60%, of the active ingredient(s). Pharmaceutical formulations for the combination therapy for enteral or parenteral administration are, for example, those in unit dosage forms, such as sugar-coated tablets, tablets, capsules or suppositories, or ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount may be reached by administration of a plurality of dosage units.

In particular, a therapeutically effective amount of each of the combination partner of the combination of the invention may be administered simultaneously or sequentially and in any order, and the components may be administered separately or as a fixed combination. For example, the method of treating a disease according to the invention may comprise (i) administration of the first agent in free or pharmaceutically acceptable salt form and (ii) administration of the second agent in free or pharmaceutically acceptable salt form, simultaneously or sequentially in any order, in jointly therapeutically effective amounts, preferably in improved therapeutically effective amounts, e.g. in daily or intermittently dosages corresponding to the amounts described herein. The individual combination partners of the combination of the invention may be administered separately at different times during the course of therapy or concurrently in divided or single combination forms. Furthermore, the term administering also encompasses the use of a pro-drug of a combination partner that convert in vivo to the combination partner as such. The instant invention is therefore to be understood as embracing all such regimens of simultaneous or alternating treatment and the term "administering" is to be interpreted accordingly.

The effective dosage of each of the combination partners employed in the combination of the invention may vary depending on the particular compound or pharmaceutical composition employed, the mode of administration, the condition being treated, the severity of the condition being treated. Thus, the dosage regimen of the combination of the invention is selected in accordance with a variety of factors including the route of administration and the renal and hepatic function of the patient. A clinician or physician of ordinary skill can readily determine and prescribe the effective amount of the single active ingredients required to alleviate, counter or arrest the progress of the condition.

Preferred suitable dosages for the compounds used in the treatment described herein are on the order of about 1 mg to about 600 mg, preferably about 3, 5, 10, 15, 20, 25, 30, 35, 40, 45, 50, 55, 60, 65, 70, 75, 80, 90, 95, 100, 120, 140, 160, 180, 200, 220, 240, 260, 280, 300, 320, 340, 360, 380, 400, 420, 440, 460, 480, 500, 520, 540, 560, 580 to about 600 mgs total.

Accordingly, in one embodiment, provided herein is a composition comprising an interferon and a compound of Formula I. In another embodiment, provided herein is a composition comprising peginterferon alfa-2a and a compound of Formula I. In an embodiment, the compound of Formula I is compound 960, compound 890, compound 893, compound 946, compound 925, compound 1080, compound 1084, compound 1085, compound 1088, compound 1100, compound 1161, compound 916, compound 1057, compound 1060, compound 1081, compound 1130, compound 1135, compound 1073, compound 1077, or compound 1076. In still another embodiment, the composition further comprises a pharmaceutically acceptable carrier.

Experimental

FIG. 1 is a line graph of viral load reduction from baseline ($Log_{10}$; ordinate) as a function of time (days; abscissa) in an uPa-SCID humanized mouse model of HBV infection. Murine subjects were administered amounts of either: capsid inhibitor only; Entecavir (ETV) only; interferon α (IFN) (PEGASYS) only; a mixture of a capsid inhibitor and Entecavir (capsid inhibitor+ETV); or a mixture of a capsid inhibitor and interferon (capsid inhibitor+IFN). Control subjects were administered dimethyl sulfoxide (DMSO) only. N=6. Surprisingly, the combination of PEGASYS with a capsid inhibitor showed improved efficacy compared to treatment with either of PEGASYS, a capsid inhibitor, ETV, or ETV in combination with PEGASYS.

Figure 2:
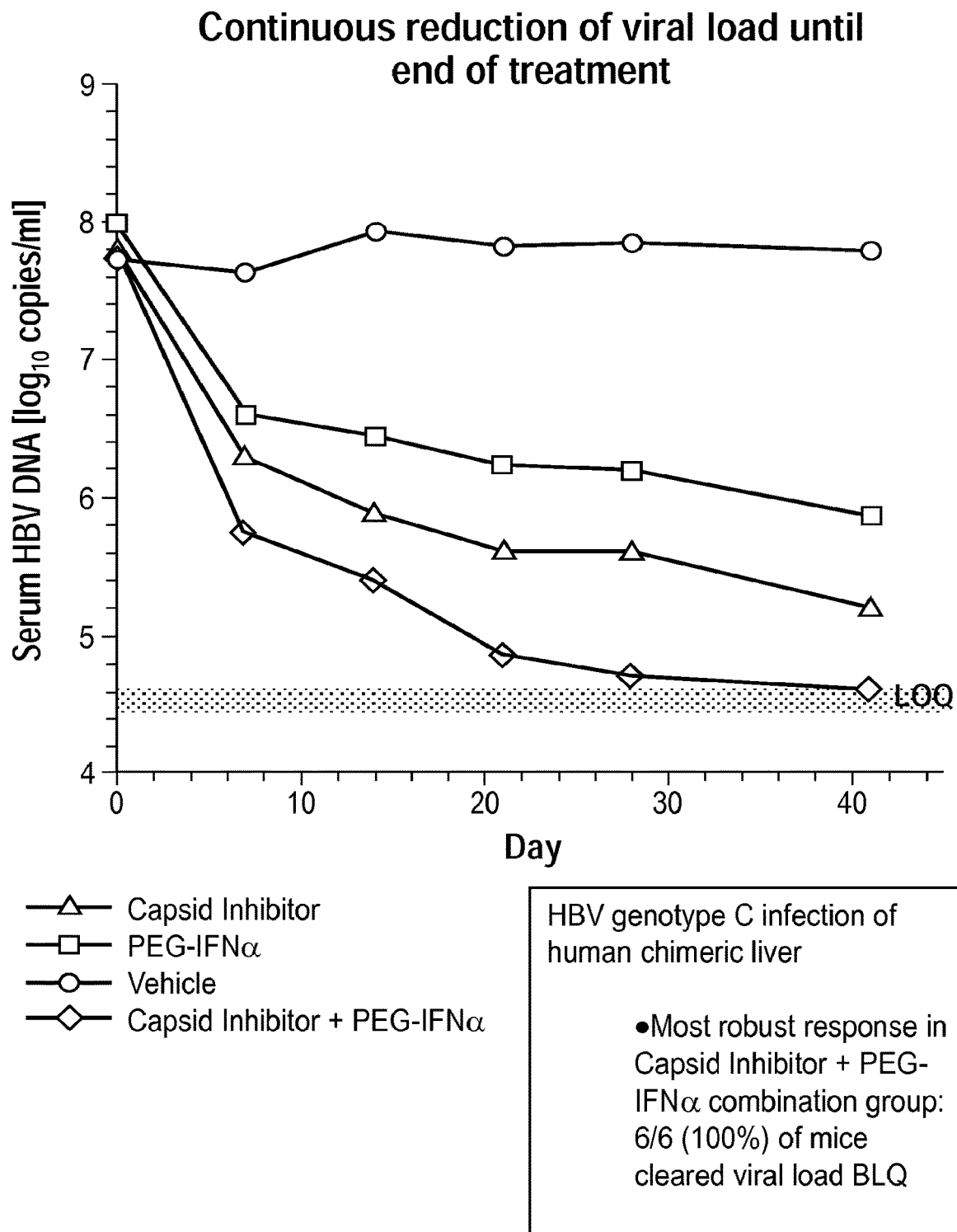
FIG. 2 is a line graph of HBV DNA ($Log_{10}$ copies/mL; ordinate) as a function of time (days; abscissa) in a murine model for HBV genotype C infection of human chimeric liver. Murine subjects were administered amounts of either: capsid inhibitor only; pegylated interferon α (PEG-IFNα) (PEGASYS); or a mixture of a capsid inhibitor and pegylated interferon α (capsid inhibitor+PEG-IFNα).

FIG. 2 is a line graph of HBV DNA (log10 copies/ml; ordinate) as a function of time (days; abscissa) in a murine model for HBV genotype C infection of human chimeric liver. Murine subjects were administered amounts of either: capsid inhibitor only; pegylated interferon α (PEG-IFN) (PEGASYS); or a mixture of a capsid inhibitor and pegylated interferon α (capsid inhibitor+PEG-IFN).

Mouse Study Protocol

| | | |
|---|---|---|
| Study Title | PK/Tolerability study of a capsid inhibitor in non-PXB grade mice and PXB-mice (4-week) | |
| Expected Study Schedule | Pre-dose blood sampling: June 21 | (Day −7) |
| | Group assignment: June 27 | (Day −1) |
| | Administration period: from June 28 (pm) to July 26 (am) | (from Day 0 to Day 27) (Day 28) |
| | Necropsy: July 26 (pm) | |
| | Study end: August 30 | |
| Objectives | The objective of this study is to evaluate the tolerability and liver toxicity of a capsid inhibitor in non-PXB grade mice and PXB-mice. | |
| Test Compounds | Identification: Capsid Inhibitor<br>Lot: PCV-CRA1.113-6<br>Nature: solid<br>Provided amount: 35 g<br>Storage conditions: store at <25 degrees C.<br>Source: Study sponsor | |
| Animals | Species: Mouse<br>Strain:<br>PXB-mouse [Genotype: eDNA-uPA$^{+/+}$/SCID, uPA$^{+/+}$: B6; 129SvEv-Plau, SCID: C.B-1711cr-scid lscid Jcl, Mouse containing human hepatocytes with an estimated replacement index of 70% or more, which is calculated based on the blood concentration of human albumin (h-Alb)]<br>non-PXB grade mouse [Genotype: eDNAuPA$^{+/+}$/SC1D,uPA$^{+/+}$: B6; 129SvEv-Plau, SCID: C.B-17/1cr-scid/scid Jcl, Mouse containing human hepatocytes with an estimated replacement index of less than 70%, which is calculated based on the blood concentration of h-Alb]<br>Number: 16 (PXB-mouse: 2, non-PXB grade mouse: 14)<br>Identification: Ear punching | |
| Acclimation | All the candidate animals will be weighed and individual health conditions will be checked. After this the mice will be acclimated to the study room for at least 7 days prior to the start of the administration. During the acclimation | |

| | | | | | | | |
|---|---|---|---|---|---|---|---|
| Group Assignment and Criteria for Animal Selection | period, health condition observations and body weight measurements will be conducted once a day for all the candidate animals.<br>On Day −7, all the candidate animals will have pre-dose blood sampling for the measurements of blood h-Alb concentration and serum ALT/AST activities. These analyses will be performed using the procedures described in the "Observations, Measurement, Sampling and Other Methods" section. The remaining serum will be stored at −80° C. until being shipped to the Sponsor.<br>On Day −1, the animals with a healthy appearance and which meet all of the criteria specified below will be assigned to the groups. To minimize variance between the groups, the group composition will be randomized based on the arithmetic mean values for body weight and geometric mean values for blood h-Alb concentration. | | | | | | |

Age: 12 to 16-weeks on Day 0
Weight: 15.6 g or more on Day −1
Blood h-Alb level: 7.0 mg/mL or more on Day −7 (for PXB-mouse) less than 7.0 mg/mL on Day −7 (for non-PXB grade mouse) Donor of hepatocytes:
  Dosing
1. Group composition 2) 1 mL of 0.5% Methocel E50 dispersion will be added drop-wise and the capsid inhibitor powder will be mixed with a pestle to make a capsid inhibitor paste.
3) A further 4 mL of 0.5% Methocel E50 dispersion will be added drop-wise whilst mixing with the pestle to make a pourable capsid inhibitor slurry. The slurry will be transferred into a tared glass vial.

| | | No. of | | Dose | | | | |
|---|---|---|---|---|---|---|---|---|
| Group | Strain | Mice (ID) | Test compound | Level ($^{111}$8/k8) | Conc. (mg/mL) | Volume (mL/k8) | Route | Frequency |
| 1 | non-PXB | 4 (101-104) | Capsid Inhibitor | 45 | 4.5 | 10 | p.o. | BID, 28 days Days 0 to 27 |
| 2 | non-PXB | 4 (201-204) | Capsid Inhibitor | 135 | 13.5 | 10 | p.o. | BID, 28-days Days 0 to 27 |
| 3 | PXB | 2 (301-302) | Capsid Inhibitor | 405 | 40.5 | 10 | p.o. | BID. 28-days Days 0 to 27 |
| | non-PXB | 2 (303-304) | Capsid Inhibitor | 405 | 40.5 | 10 | p.o. | BID, 28-days Days 0 to 27 |
| 4 | non-PXB | 4 (401-404) | Vehicle | 0 | 0 | 10 | p.o. | BID, 28-days Days 0 to 27 |

2. Preparation of 0.5% w/v Methocel E50 dispersion
  1) 1 g of Tween 80 will be weighed into a beaker (Vessel 1), and 40 mL of purified water, pre-heated to range 70° C.±5° C., will be added to Vessel 1 and the vessel will be hold at this temperature.
  2) The Tween 80 in Vessel 1 will be dissolved at range 70° C.±5° C. in 3 minutes to obtain a clear solution.
  3) 0.5 g of Methocel E50 will be weighed and added over a period of minute to the Tween 80 solution in Vessel 1, whilst mixing to create a vortex. The contents in Vessel 1 will be mixed for 5 minutes at range 70° C.±5° C. to form a consistent dispersion of Methocel E50.
  4) 50 mL of purified water at ambient temperature will be added to Vessel 1. The contents will be mixed with avoidance of excessive frothing to obtain a clear Methocel E50 dispersion. After that the Methocel E50 dispersion will be cooled to range 20° C.±3° C. whilst stirring. A cold water bath may be used to speed up the cooling rate.
  5) The contents of Vessel 1 will be transferred into a graduated measuring cylinder and adjusted with water to 100 mL. The cylinder will be sealed and the contents mixed for 1 minute by repeated inversion of the measuring cylinder.
  6) 0.5% w/v Methocel E50 dispersion will be stored at 4° C. for up to 1 week.
3. Preparation of the dose formulations
  1) CMP drug substance will be weighed and transferred into a mortar.

4) The mortar and pestle will be rinsed with 3.0 mL volumes of 0.5% Methocel E50 dispersion and the rinses will be added to the capsid inhibitor slurry.
  5) The final weight will be adjusted with 0.5% Methocel E50 dispersion to 9.33 g in the tared glass vial.
  6) Using a homogenizer (MH-1000, As One Corporation, Osaka, Japan), the white capsid inhibitor suspension will be mixed for 2 minutes at 8000 rpm.
  7) The dose formulations will be stored at room temperature for 24 hours and stirred during the dosing to ensure the homogeneity of the suspension.
4. Dose administration
  All doses will be calculated based on the individual body weights of the mice which are taken prior to the 1$^{st}$ (first) administration on the days of dosing. The dose volume factor will be 10 mL/kg. All the subject mice will receive an oral dose of the dose formulation via gavage twice a day (approx. 8 pm and 8 am; dosing times will be recorded) for 28 days from Days 0 to 27 using disposable plastic sondes (Fuchigami Kikai Co., Kyoto, Japan) and disposable 1.0 mL plastic syringes (Terumo Corporation, Tokyo, Japan).
5. Storage conditions for the remaining dose formulation
  Dose formulations will be prepared daily. After dosing, a ~100 μL sample of the remaining dose formulation will be stored at <25 degrees Celsius until the completion of all data analysis from the study, to enable the quantification of a capsid inhibitor dosed, if necessary. Any additional unused dose formulation will be disposed of according to the chemical waste disposal regulations at PhoenixBio.

| | | | Blood Volume (μL) | | | |
|---|---|---|---|---|---|---|
| | | | h-Alb | Serum Volume (μL) | | |
| Day | Time point | Subject animal | (μL) | ALT/AST | PK | |
| 0 | Pre-1$^{st}$ dose | All animals | 100 | 2 | | 40 |
| 7 | Pre-1$^{st}$ dose | #1 and #3 animals | 150 | 2 | 20 | 40 |
| | 3 hours post-1$^{st}$ dose | #2 and #4 animals | 150 | 2 | 20 | 40 |
| 14 | Pre-1$^{st}$ dose | #1 and #3 animals | 150 | 2 | 20 | 40 |
| | 3 hours post-1" dose | #2 and #4 animals | 150 | 2 | 20 | 40 |
| 21 | Pre-1$^{st}$ dose | #1 and #3 animals | 100 | 2 | | 40 |
| | 3 hours post-1$^{st}$ dose | #2 and #4 animals | 100 | 2 | | 40 |
| 27 | 1 hour Post-2$^{nd}$ dose | #1 animal | ≥400 | 2 | 20 | ≥140 |
| | 3 hours Post-2$^{nd}$ dose | #2 animal | ≥400 | 2 | 20 | ≥140 |
| | 6 hours Post-2nd dose | #3 animal | ≥400 | 2 | 20 | ≥140 |
| 28 | 12 hours Post-2$^{nd}$ dose | #4 animal | ≥400 | 2 | 20 | ≥140 |

Observations, Measurement, Sampling and Other Methods

The first day of administration will be set as Day 0. The following observations, measurements and samplings will be conducted:

1. General condition observation
Detailed observations of general condition will be conducted once a day prior to Pre-1$^{st}$ dose blood sampling, 1$^{st}$ administration on days of dosing and terminal blood sampling.

2. Body weight measurement
Individual body weights will be taken once a day prior to Pre-1° dose blood sampling, 1° administration on days of dosing and terminal blood sampling.

3. In-Life phase sample collections
A detailed blood collection schedule is as follows:

At each time point on Days 0, 7, 14 and 21, target volume of blood will be collected under isoflurane (Escain, Mylan, Osaka, Japan) anesthesia from all animals via the retro-orbital plexus/sinus using calibrated pipettes (Drummond Scientific Company, PA, USA). Two microliters (2 μL) from the collected blood will be used for these measurements. The remaining blood will be centrifuged to separate serum.

At 1 hour, 3 hours and 6 hours post-2"d dose on Day 27 and at 12 hours post 2nd dose on Day 27 (Day 28). all the subject animals will be anesthetized with isoflurane and a minimum of 400 μL of blood will be collected from each animal via the heart into syringes after which the animals will be sacrificed by cardiac puncture and exsanguination. Two microliters (2 μL) from each collected blood sample will be centrifuged to separate serum.

Necropsy will be performed after the whole blood has been collected at sacrifice. Individual whole livers will be harvested, blot-dried, divided into 6 approximately equal sized pieces, weighed, then transferred into a tube and flashed frozen in liquid nitrogen. The frozen liver samples will be stored at −80° C. until being shipped to the Sponsor.

4. Serum separation
The individual blood samples of the animals will be transferred to labeled blood collection tubes and left to coagulate at room temperature for at least 5 minutes and then centrifuged at 13200 × g, 4° C. for 3 minutes to obtain serum.
Target volume of serum from each separated serum sample will be transferred into a separate, labeled microtube.
These serum samples will be stored at −80° C. until use and being shipped to the Sponsor.

5. Laboratory investigations
The blood h-Alb concentration will be measured by PhoenixBio using latex agglutination immunonephelometry (I.X Reagent "Eiken" Alb II, Eiken Chemical Co., Ltd., Tokyo, Japan). Serum ALT/AST activities will be determined using Drichem 7000 (Fujifilm, Tokyo, Japan).

6. Adverse Events
If unexpected abnormalities such as weight loss of more than 20% of the initial body weight, moribundity or death are observed during the in-life phase, PhoenixBio will report the details of such an incident to the Appendix

APPENDIX 1

Study Schedule

| Day | Time Point | Schedule | Subject animal | Blood Volume (μL) h-Alb (μL) | | Serum Volume (μL) | | Sample List (tubes) | |
|---|---|---|---|---|---|---|---|---|---|
| | | | | | | ALT/AST | PK | Serum | Liver |
| −7 | | Pre-dose blood sampling | All the candidate | 150 | 2 | 60 | 20 | 40 | 16 |
| −1 | | Group assignment | All the candidate | | | | | | |
| 0 | Pre-1st dose | Serial blood sampling | All animals | 100 | 2 | 40 | | 40 | 16 |
| | | 1st Administration | All animals | | | | | | |
| | | 2nd Administration | All animals | | | | | | |
| | | 1st Administration | All animals | | | | | | |
| | | 2nd Administration | All animals | | | | | | |
| 2 | | 1st Administration | All animals | | | | | | |
| | | 2nd Administration | All animals | | | | | | |
| 3 | | 1st Administration | All animals | | | | | | |
| | | 2nd Administration | All animals | | | | | | |
| 4 | | 1st Administration | All animals | | | | | | |
| | | 2nd Administration | All animals | | | | | | |
| 5 | | 1st Administration | All animals | | | | | | |
| | | 2nd Administration | All animals | | | | | | |
| | | 1st Administration | All animals | | | | | | |
| | | 2nd Administration | All animals | | | | | | |
| | Pre-1st dose | Serial blood sampling | #1 and #3 animals | 150 | 2 | 60 | 20 | 40 | |
| | | 1st Administration | All animals | | | | | | |
| | 3 hours Post-1st dose | Serial blood sampling | #2 and #4 animals | 150 | 2 | 60 | 20 | 40 | 8 |
| | | 2nd Administration | All animals | | | | | | |
| | | 1st Administration | All animals | | | | | | |
| | | 2nd Administration | All animals | | | | | | |
| 9 | | 1st Administration | All animals | | | | | | |
| | | 2nd Administration | All animals | | | | | | |
| 10 | | 1st Administration | All animals | | | | | | |
| | | 2nd Administration | All animals | | | | | | |
| 11 | | 1st Administration | All animals | | | | | | |
| | | 2nd Administration | All animals | | | | | | |
| 12 | | 1st Administration | All animals | | | | | | |
| | | 2nd Administration | All animals | | | | | | |
| 13 | | 1st Administration | All animals | | | | | | |
| | | 2nd Administration | All animals | | | | | | |
| | Pre-1st d | Serial blood sampling | #1 and #3 animals | 150 | 2 | 60 | 20 | 40 | 8 |
| | | 1st Administration | All animals | | | | | | |
| 14 | 3 hours Post-1st | Serial blood sampling | #2 and #4 animals | 150 | 2 | 60 | 20 | 40 | |
| | | 2nd Administration | All animals | | | | | | |
| | | 1st Administration | All animals | | | | | | |
| 15 | | 2nd Administration | All animals | | | | | | |
| | | 1st Administration | All animals | | | | | | |
| 16 | | 2nd Administration | All animals | | | | | | |
| | | 1st Administration | All animals | | | | | | |

APPENDIX 1-continued

Study Schedule

| Day | Time Point | Schedule | Subject animal | Blood Volume (μL) h-Alb (μL) | | Serum Volume (μL) | | Sample List (tubes) | |
|---|---|---|---|---|---|---|---|---|---|
| | | | | | | ALT/AST | PK | Serum | Liver |
| 17 | | 2nd Administration | All animals | | | | | | |
| | | 1$^{st}$ Administration | All animals | | | | | | |
| 18 | | 2$^{nd}$ Administration | All animals | | | | | | |
| | | 1$^{st}$ Administration | All animals | | | | | | |
| 19 | | 2$^{nd}$ Administration | All animals | | | | | | |
| | | 1$^{st}$ Administration | All animals | | | | | | |
| 20 | | 2$^{nd}$ Administration | All animals | | | | | | |
| | Pre-1$^{st}$ dose | Serial blood sampling | #1 and 43 animals | 100 | 2 | 40 | | 40 | |
| | | 1$^{st}$ Administration | All animals | | | | | | |
| 21 | Three hours | Serial blood sampling | #2 and #4 animals | 100 | 2 | 40 | | 40 | 8 |
| | | 2$^{nd}$ Administration | All animals | | | | | | |
| | | 1$^{st}$ Administration | All animals | | | | | | |
| 22 | | 2$^{nd}$ Administration | All animals | | | | | | |
| | | 1$^{st}$ Administration | All animals | | | | | | |
| 23 | | 2$^{nd}$ Administration | All animals | | | | | | |
| | | 1$^{st}$ Administration | All animals | | | | | | |
| 24 | | 2$^{nd}$ Administration | All animals | | | | | | |
| | | 1$^{st}$ Administration | All animals | | | | | | |
| 25 | | 2$^{nd}$ Administration | All animals | | | | | | |
| | | 1$^{st}$ Administration | All animals | | | | | | |
| 26 | | 2$^{nd}$ Administration | All animals | | | | | | |
| | | 1$^{st}$ Administration | All animals | | | | | | |
| 27 | 1 hour Post-2$^{nd}$ dose | Terminal blood Necropsy | #1 animal 4 I animal | ≥400 | 2 | ≥160 | 20 | ≥140 | 24 |
| | 3 hours Post-2$^{nd}$ dose | Terminal blood Necropsy | #2 animal #2 animal | ≥400 | 2 | ≥160 | 20 | ≥140 | 24 |
| | 6 hours Post-2$^{nd}$ dose | Terminal blood Necropsy | #3 animal #3 animal | ≥400 | 2 | ≥160 | 20 | ≥140 | 24 |
| 28 | 12 hours Post-2$^{nd}$ dose | Terminal blood Necropsy | #4 animal #4 animal | ≥400 | 2 | ≥160 | 20 | ≥140 | 24 |

The invention claimed is:

1. A method of treating an HBV infection in a subject in need thereof, comprising administering to the subject a capsid assembly inhibitor and pegylated interferon, wherein the capsid assembly inhibitor is a compound of Formula I:

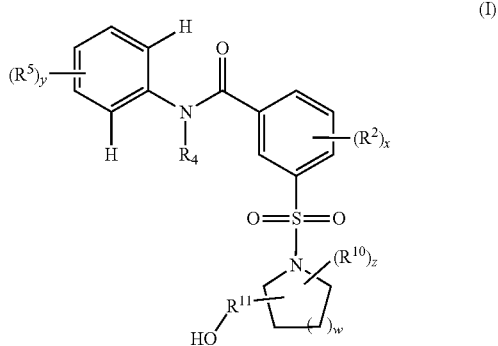

or a pharmaceutically acceptable salt thereof;
wherein
$R^4$ is H or $C_1$-$C_6$ alkyl;
wherein each $R^5$ is independently selected at each occurrence from the group consisting of $CH_3$, $C_1$-$C_6$ alkoxy, halo, —CN, —$NO_2$, -(L)$_m$-$SR^9$, -(L)$_m$-S(=O)$R^9$, -(L)$_m$-S(=O)$_2R^9$, -(L)$_m$-NHS(=O)$_2R^9$, -(L)$_m$-C(=O)$R^9$, -(L)$_m$-OC(=O)$R^9$, -(L)$_m$CO$_2R^8$, -(L)$_m$-OCO$_2R^8$, -(L)$_m$-N($R^8$)$_2$, -(L)$_m$-C(=O)N($R^8$)$_2$, -(L)$_m$-OC(=O)N($R^8$)$_2$, -(L)$_m$-NHC(=O)NH($R^8$), -(L)$_m$-NHC(=O)$R^9$, -(L)$_m$-NHC(=O)O$R^9$, -(L)$_m$-C(OH)($R^8$)$_2$, -(L)$_m$C(NH$_2$)($R^8$)$_2$, —$C_1$-$C_6$ haloalkyl, —$C_1$-$C_6$ dihaloalkyl and —$C_1$-$C_6$ trihaloalkyl;
L is independently, at each occurrence, a bivalent radical selected from —($C_1$-$C_3$ alkylene)-, —($C_3$-$C_7$ cycloalkylene)-, —($C_1$-$C_3$ alkylene)$_m$-O—($C_1$-$C_3$ alkylene)$_m$-, or —($C_1$-$C_3$ alkylene)$_m$-NH—($C_1$-$C_3$ alkylene)$_m$-;
each $R^8$ is independently, at each occurrence, H, $C_1$-$C_6$ alkyl, —$C_1$-$C_6$ haloalkyl, —$C_1$-$C_6$ dihaloalkyl, —$C_1$-$C_6$ trihaloalkyl, $C_1$-$C_6$ heteroalkyl, $C_3$-$C_{10}$ cycloalkyl, $C_3$-$C_{10}$ heterocycloalkyl, aryl, heteroaryl, —$C_1$-$C_4$ alkyl-($C_3$-$C_{10}$ cycloalkyl), —$C_1$-$C_4$ alkyl-($C_3$-$C_{10}$ heterocycloalkyl), —$C_1$-$C_4$ alkyl-(aryl), or —$C_1$-$C_4$ alkyl (heteroaryl), and wherein the alkyl, heteroalkyl, cycloalkyl, heterocycloalkyl, aryl and heteroaryl is optionally substituted with 1-5 substituents selected from $R^2$;
$R^9$ is $C_1$-$C_6$ alkyl, —$C_1$-$C_6$ haloalkyl, —$C_1$-$C_6$ dihaloalkyl, —$C_1$-$C_6$ trihaloalkyl, $C_1$-$C_6$ heteroalkyl, $C_3$-$C_{10}$ cycloalkyl, a $C_3$-$C_{10}$ heterocycloalkyl, aryl, heteroaryl, —$C_1$-$C_4$ alkyl-($C_3$-$C_{10}$ cycloalkyl), —$C_1$-$C_4$ alkyl-($C_3$-$C_{10}$ heterocycloalkyl), —$C_1$-$C_4$ alkyl-(aryl), or —$C_1$-$C_4$ alkyl-(heteroaryl), and wherein the alkyl, heteroalkyl, cycloalkyl, heterocycloalkyl, aryl or heteroaryl ring is optionally substituted with 0-5 substituents selected from $R^2$;
$R^{10}$ is OH, $C_1$-$C_6$ alkyl, $C_1$-$C_6$ alkyl-OH, —$C_1$-$C_6$ haloalkyl, —$C_1$-$C_6$ dihaloalkyl, —$C_1$-$C_6$ trihaloalkyl, $C_1$-$C_6$ heteroalkyl, $C_3$-$C_{10}$ cycloalkyl, a $C_3$-$C_{10}$ heterocycloalkyl, aryl, heteroaryl, —$C_1$-$C_4$ alkyl-($C_3$-$C_{10}$ cycloalkyl), —$C_1$-$C_4$ alkyl-($C_3$-$C_{10}$ heterocycloalkyl), —$C_1$-$C_4$ alkyl-(aryl), or —$C_1$-$C_4$ alkyl-(heteroaryl), and wherein the alkyl, heteroalkyl, cycloalkyl, heterocycloalkyl, aryl or heteroaryl ring is optionally substituted with 1-5 substituents selected from $R^2$;
$R^{11}$ is a bond or $C_1$-$C_3$ alkylene, wherein the $C_1$-$C_3$ alkylene is optionally substituted with 1-3 substituents selected from $R^2$;
$R^2$ is independently selected at each occurrence from the group consisting of OH, halo, —CN, —$NO_2$, —$C_1$-$C_6$ alkyl, —$C_1$-$C_6$ alkoxy, —$C_1$-$C_6$ haloalkyl, —$C_1$-$C_6$ dihaloalkyl, —$C_1$-$C_6$ trihaloalkyl, —$C_1$-$C_6$ heteroalkyl, and C(O) —$C_1$-$C_6$ alkyl;
w is 0, 1 or 2;
each occurrence of x is independently selected from the group consisting of 0, 1, 2, 3 and 4;
each occurrence of y is independently selected from the group consisting of 1, 2, and 3;
each occurrence of z is independently selected from the group consisting of 0, 1, 2, and 3;
each occurrence of m is independently 0, 1 or 2.

2. The method of claim 1, wherein the pegylated interferon is selected from the group consisting of peginterferon-alpha 2a, peginterferon alpha-2b, peginterferon beta-1a, peginterferon lambda-1, DA-3021, and PEG-Infergen.

3. The method of claim 2, wherein the pegylated interferon is selected from the group consisting of peginterferon alpha-2a, peginterferon alpha-2b, peginterferon alpha-1a, and peginterferon lambda-1.

4. The method of claim 3, wherein the pegylated interferon is peginterferon alpha-2a.

5. The method of claim 1, wherein the pegylated interferon and compound of Formula I are in a single formulation or unit dosage form.

6. The method of claim 5, further comprising a pharmaceutically acceptable carrier.

7. The method of claim 1, wherein the pegylated interferon and compound of Formula I are administered separately.

8. The method of claim 1, wherein the subject is human.

9. The method of claim 1, wherein the treatment comprises administering the pegylated interferon and compound of Formula I at substantially the same time.

10. The method of claim 1, wherein the treatment comprises administering the pegylated interferon and compound of Formula I at different times.

11. The method of claim 10, wherein the pegylated interferon is administered to the subject, followed by administration of a compound of Formula I.

12. The method of claim 10, wherein the compound of Formula I is administered to the subject, followed by administration of the pegylated interferon.

13. The method of claim 10, wherein the pegylated interferon and compound of Formula I are in separate formulations or unit dosage forms.

14. The method of claim 1, wherein the pegylated interferon and compound of Formula I are administered at dosages that would not be effective when one or both of the pegylated interferon and compound of Formula I are administered alone, but which amounts are effective in combination.

15. A composition comprising pegylated interferon and a compound of Formula I:

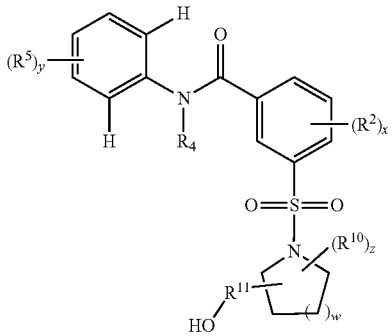

(I)

or a pharmaceutically acceptable salt thereof;
wherein
$R^4$ is H or $C_1$-$C_6$ alkyl;
wherein each $R^5$ is independently selected at each occurrence from the group consisting of $CH_3$, $C_1$-$C_6$ alkoxy, halo, —CN, —$NO_2$, -(L)$_m$-$SR^9$, -(L)$_m$-S(=O)$R^9$, -(L)$_m$-S(=O)$_2R^9$, -(L)$_m$-NHS(=O)$_2R^9$, -(L)$_m$-C(=O)$R^9$, -(L)$_m$-OC(=O)$R^9$, -(L)$_m$-$CO_2R^8$, -(L)$_m$-$OCO_2R^8$, -(L)$_m$-N($R^8$)$_2$, -(L)$_m$-C(=O)N($R^8$)$_2$, -(L)$_m$-OC(=O)N($R^8$)$_2$, -(L)$_m$-NHC(=O)NH($R^8$), -(L)$_m$-NHC(=O)$R^9$, -(L)$_m$-NHC(=O)O$R^9$, -(L)$_m$-C(OH)($R^8$)$_2$, -(L)$_m$C($NH_2$)($R^8$)$_2$, —$C_1$-$C_6$ haloalkyl, —$C_1$-$C_6$ dihaloalkyl and —$C_1$-$C_6$ trihaloalkyl;
L is independently, at each occurrence, a bivalent radical selected from —($C_1$-$C_3$ alkylene)-, —($C_3$-$C_7$ cycloalkylene)-, —($C_1$-$C_3$ alkylene)$_m$-O—($C_1$-$C_3$ alkylene)$_m$-, or —($C_1$-$C_3$ alkylene)$_m$-NH—($C_1$-$C_3$ alkylene)$_m$-;
each $R^8$ is independently, at each occurrence, H, $C_1$-$C_6$ alkyl, —$C_1$-$C_6$ haloalkyl, —$C_1$-$C_6$ dihaloalkyl, —$C_1$-$C_6$ trihaloalkyl, $C_1$-$C_6$ heteroalkyl, $C_3$-$C_{10}$ cycloalkyl, $C_3$-$C_{10}$ heterocycloalkyl, aryl, heteroaryl, —$C_1$-$C_4$ alkyl-($C_3$-$C_{10}$ cycloalkyl), —$C_1$-$C_4$ alkyl-($C_3$-$C_{10}$ heterocycloalkyl), —$C_1$-$C_4$ alkyl-(aryl), or —$C_1$-$C_4$ alkyl (heteroaryl), and wherein the alkyl, heteroalkyl, cycloalkyl, heterocycloalkyl, aryl and heteroaryl is optionally substituted with 1-5 substituents selected from $R^2$;
$R^9$ is $C_1$-$C_6$ alkyl, —$C_1$-$C_6$ haloalkyl, —$C_1$-$C_6$ dihaloalkyl, —$C_1$-$C_6$ trihaloalkyl, $C_1$-$C_6$ heteroalkyl, $C_3$-$C_{10}$ cycloalkyl, a $C_3$-$C_{10}$ heterocycloalkyl, aryl, heteroaryl, —$C_1$-$C_4$ alkyl-($C_3$-$C_{10}$ cycloalkyl), —$C_1$-$C_4$ alkyl-($C_3$-$C_{10}$ heterocycloalkyl), —$C_1$-$C_4$ alkyl-(aryl), or —$C_1$-$C_4$ alkyl-(heteroaryl), and wherein the alkyl, heteroalkyl, cycloalkyl, heterocycloalkyl, aryl or heteroaryl ring is optionally substituted with 0-5 substituents selected from $R^2$;
$R^{10}$ is OH, $C_1$-$C_6$ alkyl, $C_1$-$C_6$ alkyl-OH, —$C_1$-$C_6$ haloalkyl, —$C_1$-$C_6$ dihaloalkyl, —$C_1$-$C_6$ trihaloalkyl, $C_1$-$C_6$ heteroalkyl, $C_3$-$C_{10}$ cycloalkyl, a $C_3$-$C_{10}$ heterocycloalkyl, aryl, heteroaryl, —$C_1$-$C_4$ alkyl-($C_3$-$C_{10}$ cycloalkyl), —$C_1$-$C_4$ alkyl-($C_3$-$C_{10}$ heterocycloalkyl), —$C_1$-$C_4$ alkyl-(aryl), or —$C_1$-$C_4$ alkyl-(heteroaryl), and wherein the alkyl, heteroalkyl, cycloalkyl, heterocycloalkyl, aryl or heteroaryl ring is optionally substituted with 1-5 substituents selected from $R^2$;
$R^{11}$ is a bond or $C_1$-$C_3$ alkylene, wherein the $C_1$-$C_3$ alkylene is optionally substituted with 1-3 substituents selected from $R^2$;
$R^2$ is independently selected at each occurrence from the group consisting of OH, halo, —CN, —$NO_2$, —$C_1$-$C_6$ alkyl, —$C_1$-$C_6$ alkoxy, —$C_1$-$C_6$ haloalkyl, —$C_1$-$C_6$ dihaloalkyl, —$C_1$-$C_6$ trihaloalkyl, —$C_1$-$C_6$ heteroalkyl, and C(O)—$C_1$-$C_6$ alkyl;
w is 0, 1 or 2;
each occurrence of x is independently selected from the group consisting of 0, 1, 2, 3 and 4;
each occurrence of y is independently selected from the group consisting of 1, 2, and 3;
each occurrence of z is independently selected from the group consisting of 0, 1, 2, and 3;
each occurrence of m is independently 0, 1 or 2.

16. A method of treating an HBV infection in a subject in need thereof comprising administering to the subject an effective amount of the composition of claim 15.

* * * * *

UNITED STATES PATENT AND TRADEMARK OFFICE
CERTIFICATE OF CORRECTION

PATENT NO. : 10,632,112 B2
APPLICATION NO. : 16/235210
DATED : April 28, 2020
INVENTOR(S) : George D. Hartman Page 1 of 1

It is certified that error appears in the above-identified patent and that said Letters Patent is hereby corrected as shown below:

In the Claims

Claim 3, Column 42, Line 28, should read:
-- alpha-2a, peginterferon alpha-2b, peginterferon beta-1a, --

Signed and Sealed this
Fourteenth Day of July, 2020

Andrei Iancu
*Director of the United States Patent and Trademark Office*